: US008674291B2

(12) United States Patent
Ghoshal et al.

(10) Patent No.: US 8,674,291 B2
(45) Date of Patent: Mar. 18, 2014

(54) MASS SPECTROMETRY ASSAY FOR CONGENITAL ADRENAL HYPERPLASIA

(71) Applicant: Quest Diagnostics Investments Incorporated, Wilmington, DE (US)

(72) Inventors: Amit Ghoshal, Ladera Ranch, CA (US); Nigel J. Clarke, Oceanside, CA (US); Mildred M. Goldman, Laguna Niguel, CA (US)

(73) Assignee: Quest Diagnostics Investments Inc., Wilmington, DE (US)

( * ) Notice: Subject to any disclaimer, the term of this patent is extended or adjusted under 35 U.S.C. 154(b) by 0 days.

(21) Appl. No.: 14/026,793

(22) Filed: Sep. 13, 2013

(65) Prior Publication Data

US 2014/0014832 A1 Jan. 16, 2014

Related U.S. Application Data

(63) Continuation of application No. 13/851,621, filed on Mar. 27, 2013, now abandoned, which is a continuation of application No. 13/417,093, filed on Mar. 9, 2012, now Pat. No. 8,415,616, which is a continuation of application No. 12/645,393, filed on Dec. 22, 2009, now Pat. No. 8,153,962.

(60) Provisional application No. 61/140,824, filed on Dec. 24, 2008.

(51) Int. Cl.
*G01N 31/00* (2006.01)
*C12Q 1/02* (2006.01)
*G01N 33/53* (2006.01)
*G01N 33/74* (2006.01)
*G01N 33/68* (2006.01)
*C12Q 1/68* (2006.01)

(52) U.S. Cl.
CPC ............ *G01N 33/743* (2013.01); *G01N 33/689* (2013.01); *G01N 33/6848* (2013.01); *C12Q 1/6872* (2013.01)
USPC ........... 250/282; 250/281; 250/284; 250/286; 250/287; 250/288; 435/7.1

(58) Field of Classification Search
CPC ............ G01N 33/743; G01N 33/6848; G01N 33/689; G01N 2800/368; G01N 2800/04; G01N 2333/723; G01N 33/74; H01J 49/004; C12Q 1/6872
USPC ................. 250/281, 282, 284, 286, 287, 288; 435/7.1
See application file for complete search history.

(56) References Cited

U.S. PATENT DOCUMENTS 5,772,874 A 6/1998 Quinn et al.
5,795,469 A 8/1998 Quinn et al.
(Continued)

OTHER PUBLICATIONS

Alvarez-Sanchez et al, Automated solid-phase extraction for concentration and clean-up of female steroid hormones prior to liquid chromatography-electrospray ionization-tandem mass spectrometry: an approach to lipidomics, Chromatogr A., 1207(1-2):46-54.

(Continued)

*Primary Examiner* — David A Vanore
(74) *Attorney, Agent, or Firm* — Quest Diagnostics, Inc.

(57) ABSTRACT

Methods are provided for detecting the amount of one or more CAH panel analytes (i.e., pregnenolone, 17-OH pregnenolone, progesterone, 17-OH progesterone, dehydroepiandrosterone (DHEA), androstenedione, testosterone, deoxycorticosterone, 11-deoxycortisol, and cortisol) in a sample by mass spectrometry. The methods generally involve ionizing one or more CAH panel analytes in a sample and quantifying the generated ions to determine the amount of one or more CAH panel analytes in the sample. In methods where amounts of multiple CAH panel analytes are detected, the amounts of multiple analytes are detected in the same sample injection.

20 Claims, 25 Drawing Sheets

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koster |
| 6,660,726 | B2 | 12/2003 | Hill et al. |
| 6,800,489 | B2 | 10/2004 | Dooley |
| 6,977,143 | B1 | 12/2005 | Caulfield et al. |
| 7,348,137 | B2 | 3/2008 | Caulfield et al. |
| 7,439,026 | B2 * | 10/2008 | Pandian et al. ............... 435/7.1 |
| 7,473,560 | B2 | 1/2009 | Soldin |
| 7,804,063 | B2 | 9/2010 | Ghoshal et al. |
| 7,893,399 | B2 * | 2/2011 | Ghoshal et al. ............. 250/282 |
| 7,923,257 | B2 * | 4/2011 | Cerda et al. ..................... 436/89 |
| 7,935,921 | B2 | 5/2011 | Grant et al. |
| 8,153,962 | B2 | 4/2012 | Ghoshal et al. |
| 8,283,627 | B2 * | 10/2012 | Ghoshal et al. ............. 250/282 |
| 8,293,540 | B2 * | 10/2012 | Holmquist et al. .......... 436/173 |
| 8,410,428 | B2 * | 4/2013 | Ghoshal et al. ............. 250/282 |
| 8,563,922 | B2 * | 10/2013 | Clarke et al. ................. 250/282 |
| 2003/0228704 | A1 | 12/2003 | Dooley |
| 2005/0020552 | A1 | 1/2005 | Aschkenasy et al. |
| 2008/0128606 | A1 * | 6/2008 | Grant et al. ................... 250/282 |
| 2009/0104624 | A1 * | 4/2009 | Pandian et al. ............... 435/7.1 |
| 2009/0312366 | A1 | 12/2009 | Bos |
| 2010/0047849 | A1 | 2/2010 | Caulfield et al. |
| 2010/0059671 | A1 * | 3/2010 | Ghoshal et al. ............. 250/282 |
| 2010/0084546 | A1 * | 4/2010 | Ghoshal et al. ............. 250/282 |
| 2010/0227412 | A1 | 9/2010 | Cerda |
| 2011/0006197 | A1 | 1/2011 | Ghoshal et al. |
| 2011/0107820 | A1 | 5/2011 | Kushnir et al. |
| 2011/0147583 | A1 | 6/2011 | Ghoshal et al. |

OTHER PUBLICATIONS

Andersson et al., "Effects of ethanol on steroid profiles in the rat testis", Biochimica et Biophysica Acta (BBA)—Lipids and Lipid Metabolism, vol. 876, Issue 2, 1986, pp. 352-357.

Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom, 14:967-73 (2000).

Caruso et al., "Evaluation of neuroactive steroid levels by liquid chromatography-tandem mass spectrometry in central and peripheral nervous system: Effect of diabetes", Neurochemistry International, vol. 52, Issues 4-5, 2008, pp. 560-568.

Carvalho, V., et al., Simultaneous quantitation of seven enogenous C-21 adrenal steroids by liquid chromatography tandem mass spectrometry in human serum. Chromatogr A 872:154-61, 2008.

Chia, et al., "Changes in cytochrome P450 side chain cleavage expression in the rat hippocampus after kainate injury", Experimental Brain Research, vol. 186, Issue 1, 2008, pp. 143-149.

Diaz-Cruz et al, Determination of estrogens and progestogens by mass spectrometric techniques (GC/MS, LC/MS and LC/MS/MS), J. Mass Spectrom., 38:912-923 (2003).

Dorgan et al., Measurement of steroid sex hormones in serum: a comparison of radioimmunoassay and mass spectrometry, Steroids, 67: 151-8 (2002).

Extended European Search Report issued Nov. 6, 2012 in European Patent Application No. 09835800.5.

International Search Report for PCT Application No. PCT/US2009/069305 Mailed Mar. 3, 2010.

Janzen, M., et al., Newborn screening for congenital adrenal hyperplasia: Additional steroid profile using liquid chromatography-tandem mass spectrometry. J. Clin Endocrinol Metab 92:2581-9, 2007.

Kushnir, M., et al., Development and performance evaluation of a tandem mass spectrometry assay for 4 adrenal steroids. Clinical Chemistry 52:1559-67, 2006.

Lacey, et al., Improved specificity of newborn screening for congenital adrena; hyperplasia by second-tier steroid profiling using tandem mass spectrometry. Clinical Chemistry 50:621-5, 2004.

Merchant and Weinberger, Recent advancements in surface-enhanced laser desorption/ionization-time of flight-mass spectrometry. Electrophoresis 21: 1164-1177 (2000).

Minutti, C., et al., Steroid profiling by tandem mass spectrometry improves the positive predictive value of newborn screening for congenital adrenal hyperplasia. J. Clin Endocrinol Metab, 89:3687-93, 2004.

Non-Final Office Action in U.S. Appl. No. 12/645,393 dated Jun. 29, 2011.

Non-Final Office Action in U.S. Appl. No. 13/417,093 dated Aug. 23, 2012.

Notice of Allowance in U.S. Appl. No. 12/645,393 dated Dec. 5, 2011.

Notice of Allowance in U.S. Appl. No. 13/417,093 dated Dec. 13, 2012.

Notice of Allowance in U.S. Appl. No. 13/851,621 dated Jun. 25, 2013.

Rauh, M., et al., Automated, fast and sensitive quantification of 17a-hydroxy-progesterone, androstenedione and testosterone by tandem mass spectrometry with on-line extraction. Steroids 71:450-8, 2006.

Robb et al., Atmospheric Pressure Photoionization: An Ionization Method for Liquid Chromatography-Mass Spectrometry. Anal. Chem. 72(15):3653-3659 (2000).

Shindo, N., et al., Identification of 17-hydroxyprogesterone and other steroid hormones in saliva from a normal child and patients with congenital adrenal hyperplasia by plasmaspray liquid chromatography/mass spectrometry. Biomedical Chromatogr 4:171-4, 1990.

Wolthers et al., "Detection of 3β-hydroxysteroid dehydrogenase deficiency in a newborn by means of urinary steroid analysis", Clinica Chimica Acta, vol. 169, Issue 1, 1987, pp. 109-116.

Wright et al., Proteinchip® surface enhanced laser desorption/ionization (SELDI) mass spectrometry: a novel protein biochip technology for detection of prostate cancer biomarkers in complex protein mixtures, Prostate Cancer and Prostatic Diseases, 2:264-276 (1999).

Wudy et al., "Determination of 17α-hydroxypregnenolone in human plasma by routine isotope dilution mass spectrometry using benchtop gas chromatography-mass selective detection", Steroids, vol. 66, Issue 10, 2001, pp. 759-762.

Zimmer et al., Comparison of turbulent-flow chromatography with automated solid-phase extraction in 96-well plates and liquid-liquid extraction used as plasma sample preparation techniques for liquid chromatography-tandem mass spectrometry. J Chromatogr A, 854: 23-35 (1999).

* cited by examiner

Figure 1 A-B
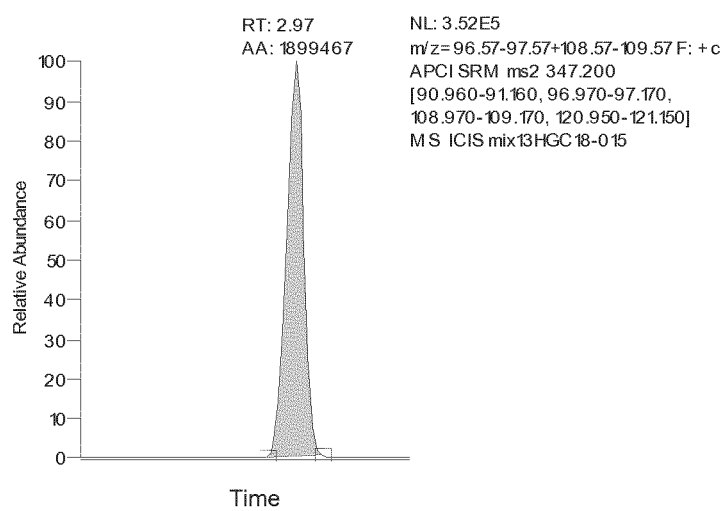
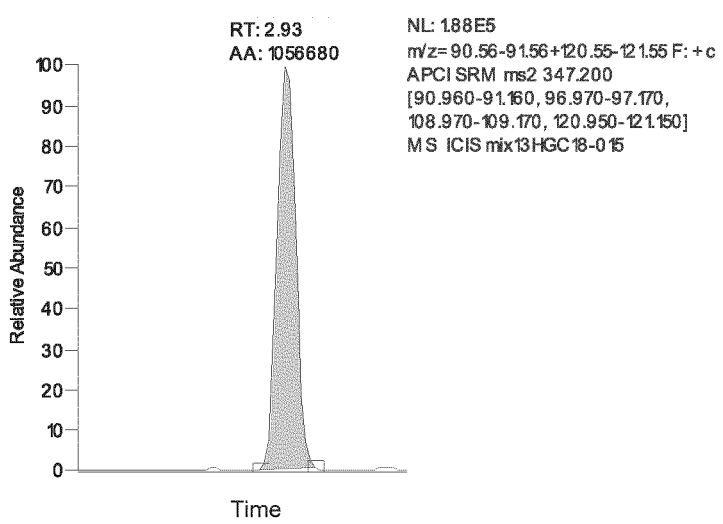

Figure 1C-D
C
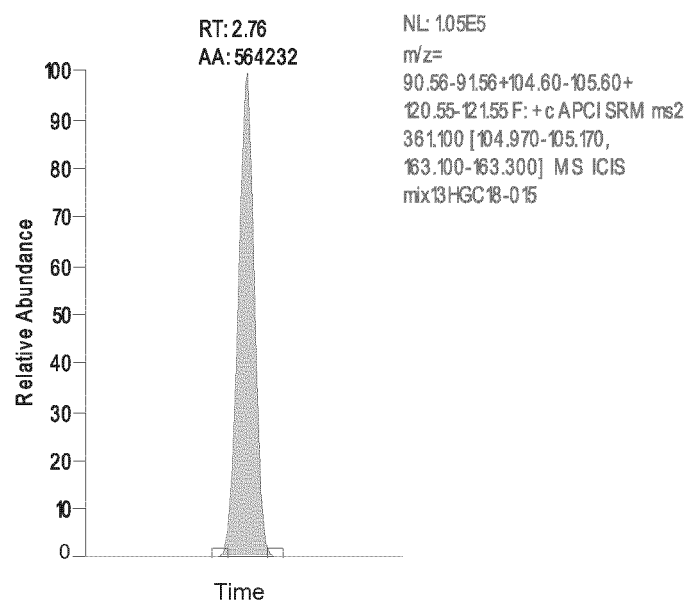
D
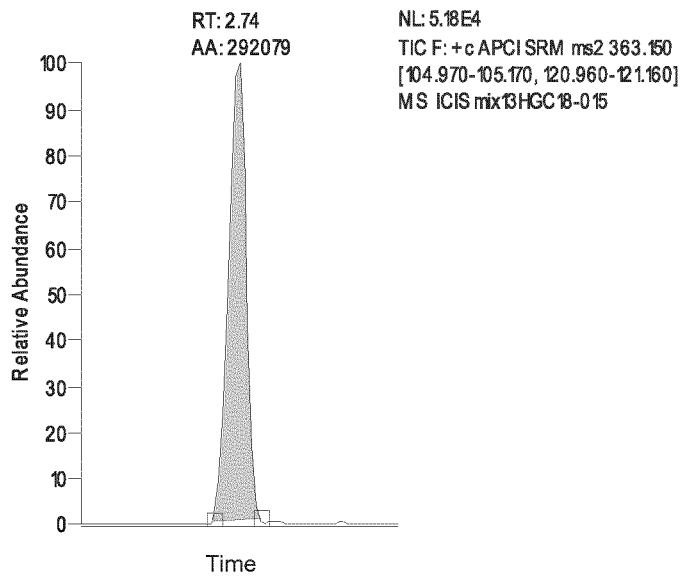

Figure 1E-F
E
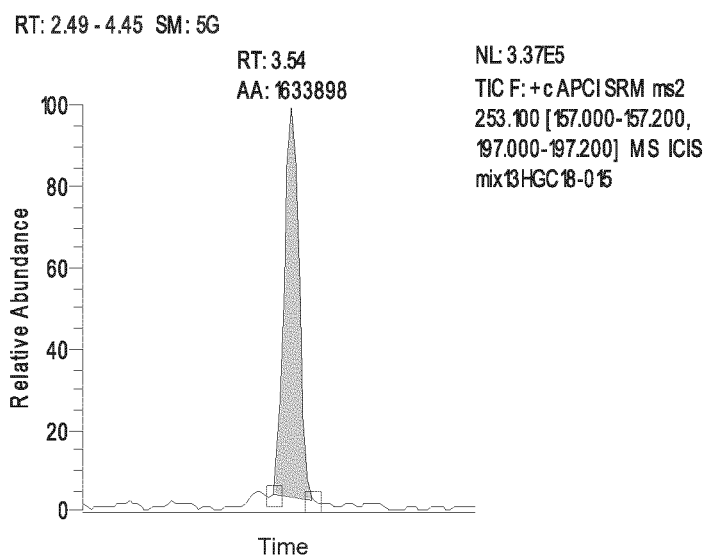
F
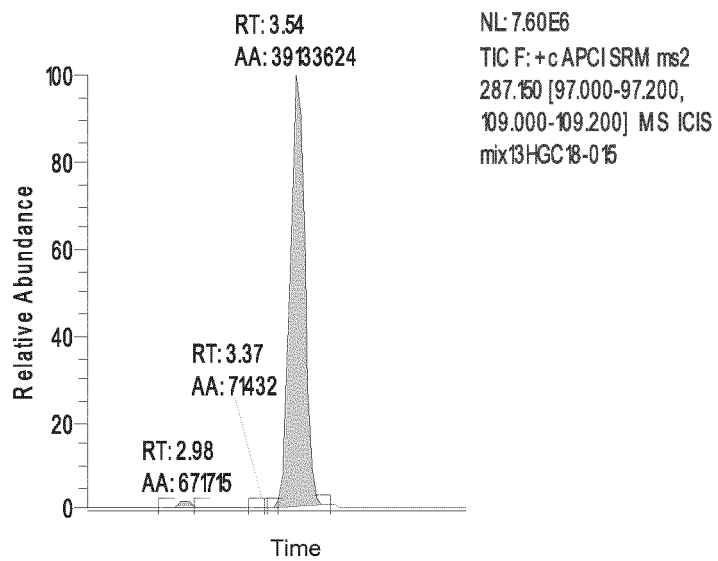

Figure 1G-H
G
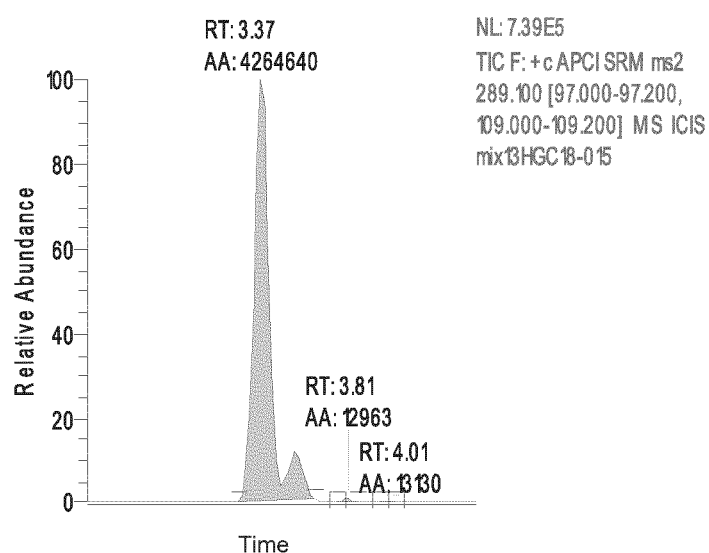
H
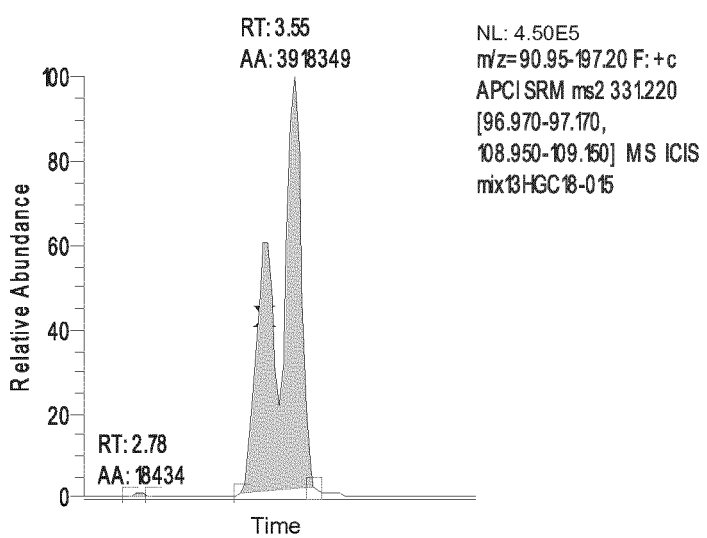

Figure 1I-J
I
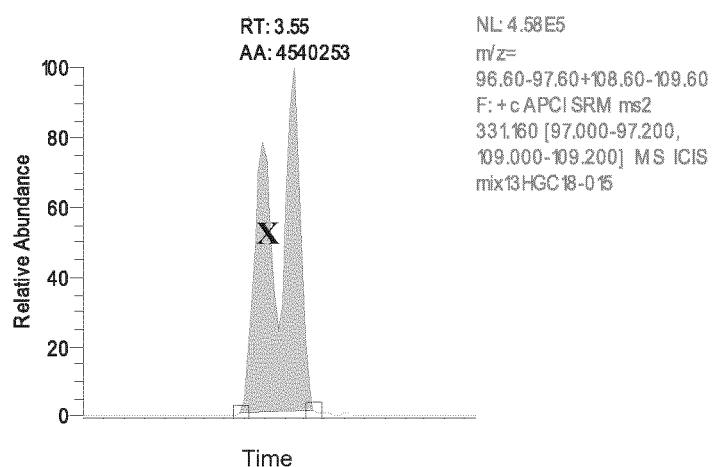
J
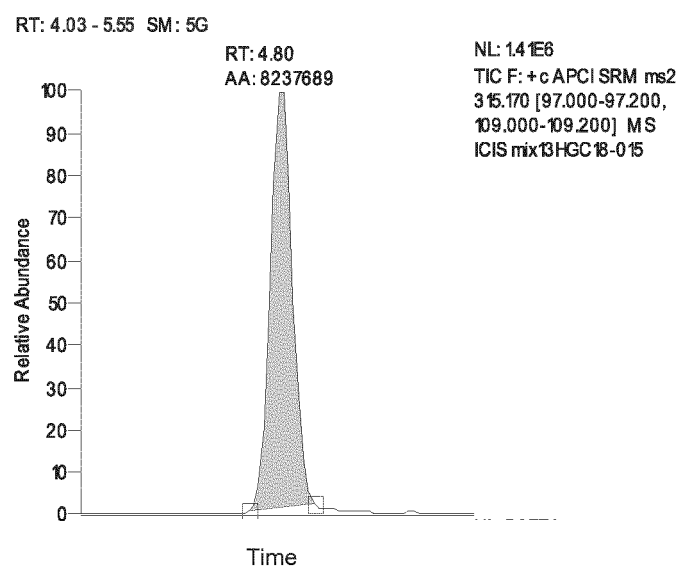

Figure 1K-L
K
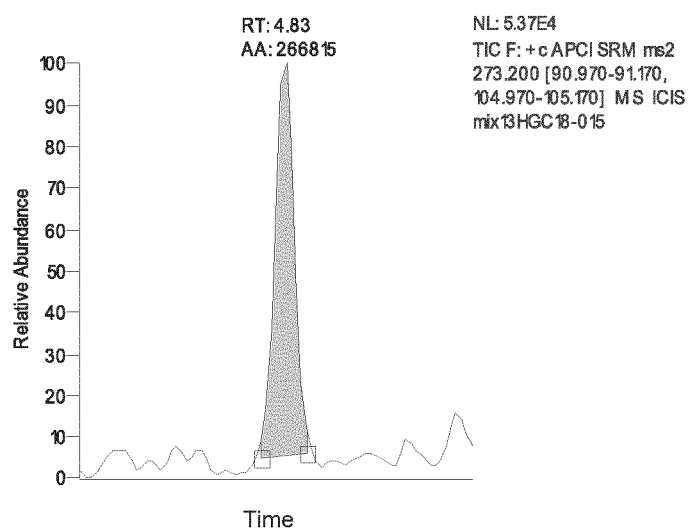
L
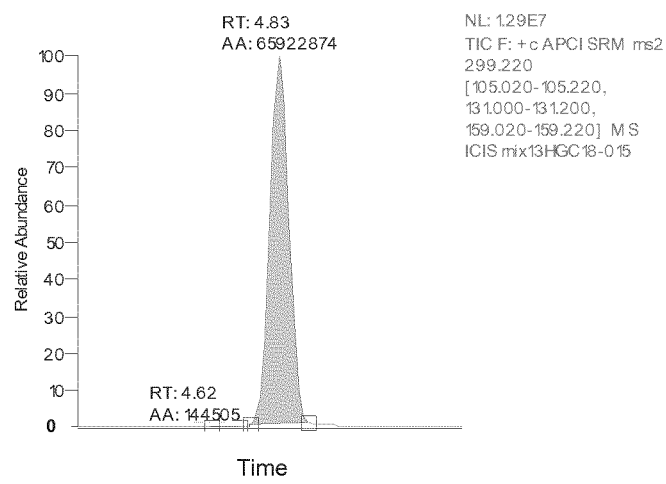

Figure 15A-B
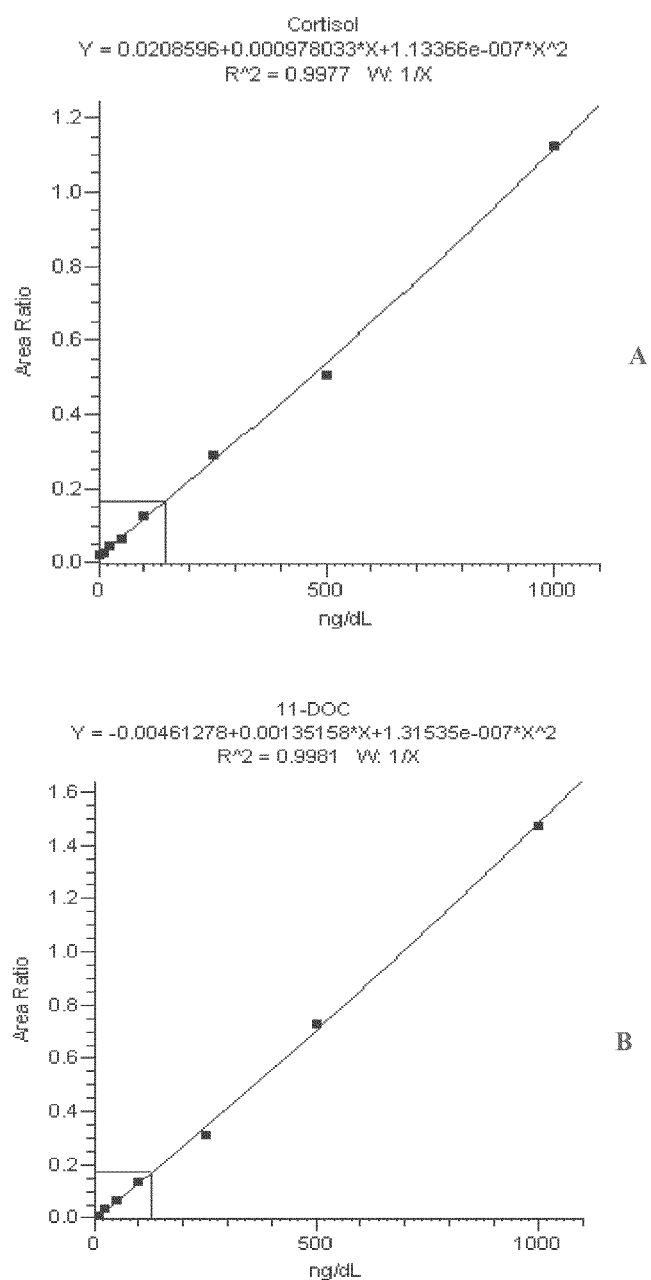

Figure 15C-D
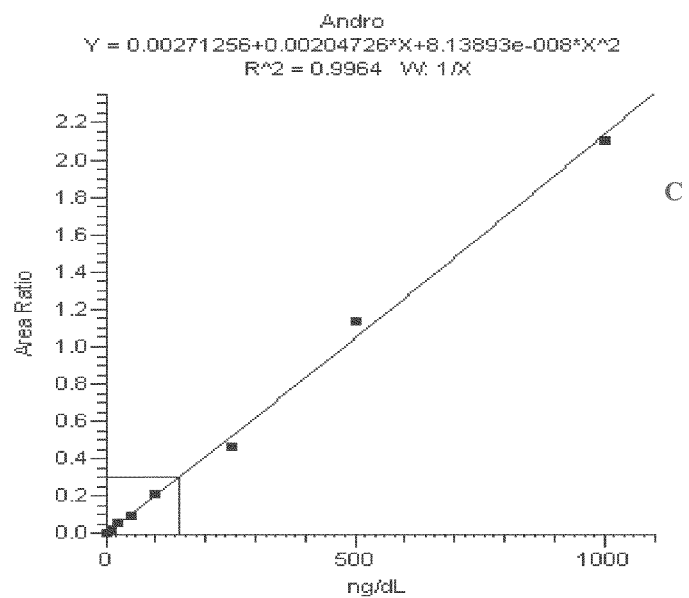
C
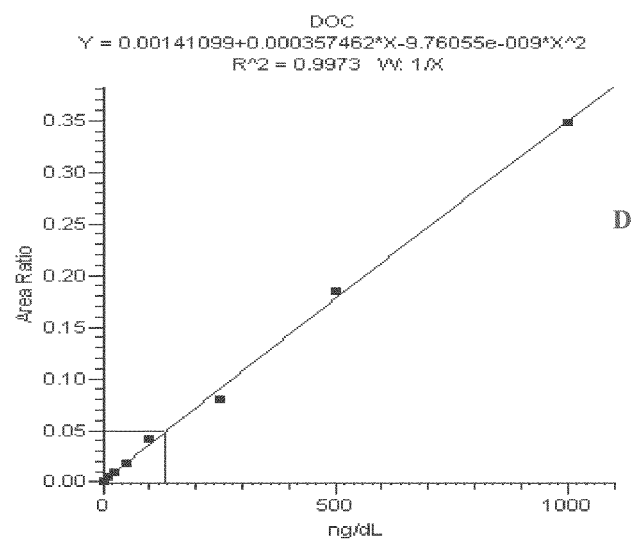
D

Figure 15E-F
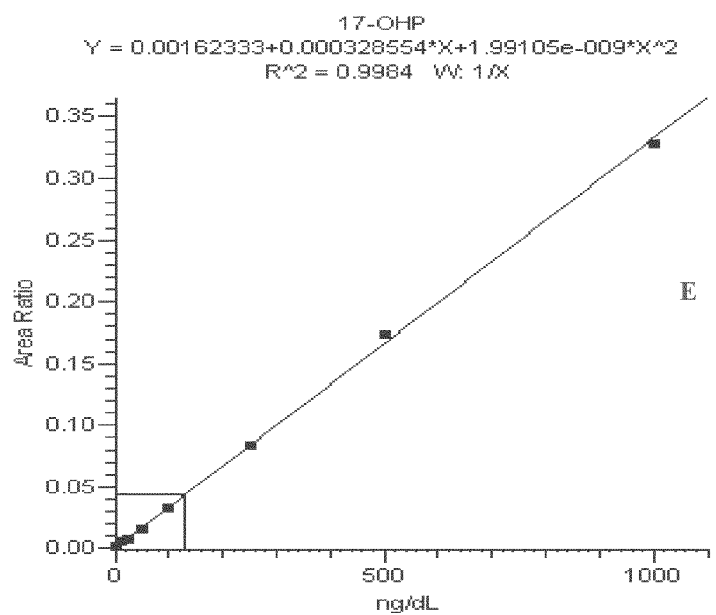
E
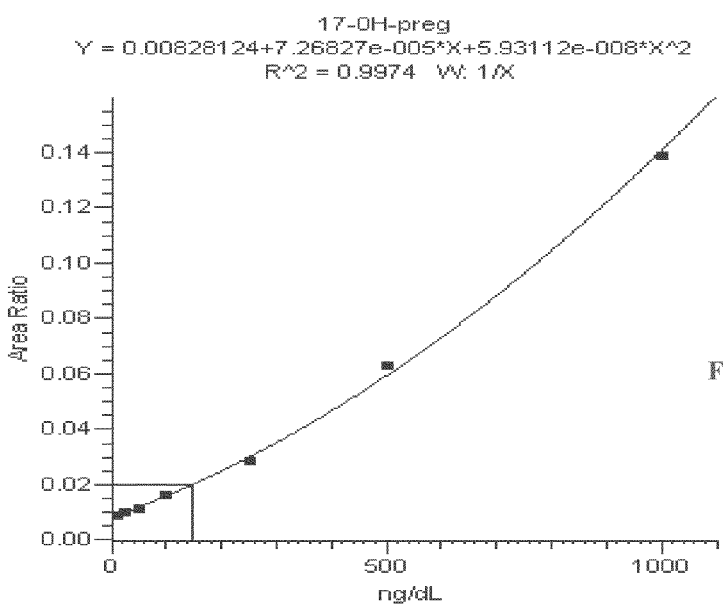
F

Figure 15G-H
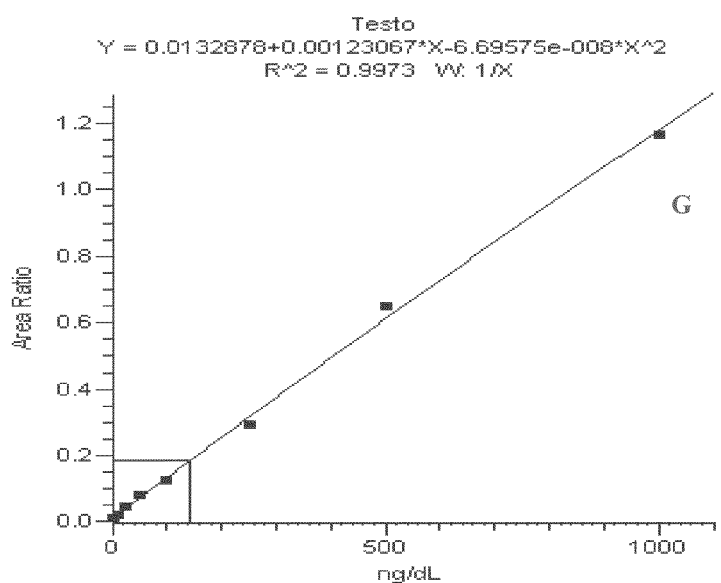
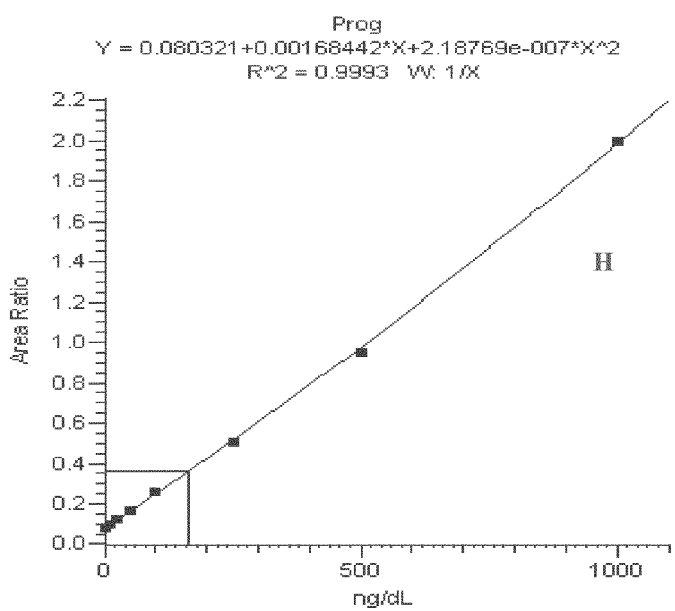

Figure 15I-J
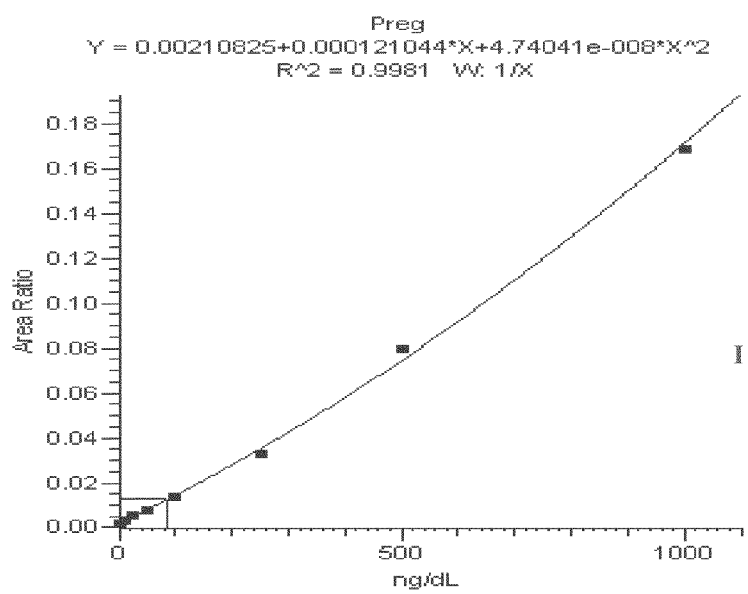
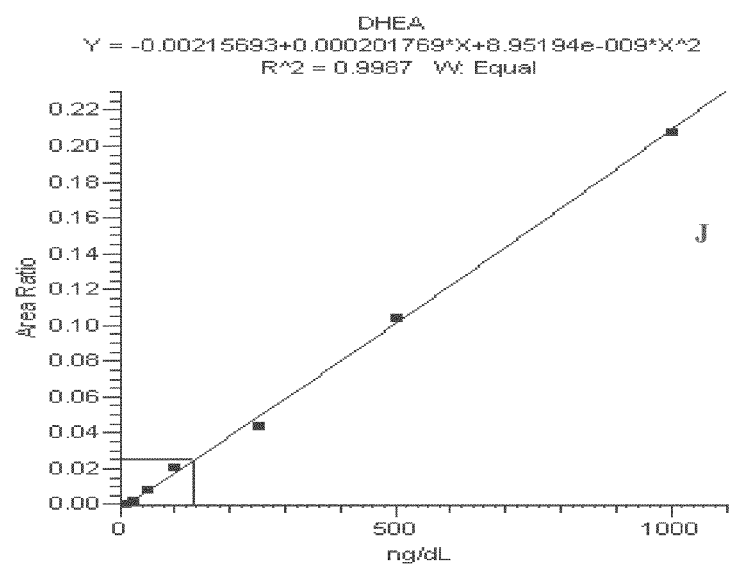

MASS SPECTROMETRY ASSAY FOR CONGENITAL ADRENAL HYPERPLASIA

CROSS REFERENCE TO RELATED PATENT APPLICATIONS

This application is a continuation of U.S. application Ser. No. 13/851,621, filed Mar. 27, 2013, which is a continuation of U.S. application Ser. No. 13/417,093, filed Mar. 9, 2012, now U.S. Pat. No. 8,415,616, which is a continuation of U.S. application Ser. No. 12/645,393, filed Dec. 22, 2009, now U.S. Pat. No. 8,153,962, which claims priority to U.S. Provisional Application. No. 61/140,824, filed Dec. 24, 2008, the contents of each of which are hereby incorporated by reference in their entirety.

FIELD OF THE INVENTION

The invention relates to methods for measurement of certain analytes that may indicate congenital adrenal hyperplasia, in particular by tandem mass spectrometry.

BACKGROUND OF THE INVENTION

The following description of the background of the invention is provided simply as an aid in understanding the invention and is not admitted to describe or constitute prior art to the invention.

Congenital Adrenal Hyperplasia (CAH) is a family of inherited disorders affecting the adrenal glands. The most common form is 21-hydroxylase deficiency (21-OHD), which is inherited in severe or mild forms. The severe form, called Classical CAH, is usually detected in the newborn period or in early childhood. The milder form, called Nonclassical CAH (NCAH), may cause symptoms at anytime from infancy through adulthood. NCAH is a much more common disorder than Classical CAH. Fortunately, CAH can be managed with medication and, with adequate care, affected individuals go on to live normal lives.

Cortisol is a steroid produced by the adrenal glands. Cortisol is used in the body to respond to physical and emotional stress, and maintain adequate energy supply and blood sugar levels.

The adrenal glands are controlled by the pituitary gland, a small pea-sized gland at the base of the brain. In health individuals, the pituitary gland releases adrenocorticotropic hormone (ACTH) when there is insufficient cortisol present in the bloodstream. ACTH stimulates the adrenals to produce more cortisol. However, those with CAH have insufficient amounts of the enzyme 21-hydroxylase, which is needed to convert the precursor 17-hydroxyprogesterone (17-OHP) into cortisol. As a result, the pituitary gland continues to sense the need for cortisol and pumps out more ACTH. This leads to an overabundance of 17-OHP, which is then converted in the adrenals into excess androgens (masculinizing steroid hormones).

As such, an individual may be diagnosed with CAH by determining the circulating levels of the affected steroid hormones. Additionally, an individual with CAH may be monitored by tracking circulating levels of these hormones.

Detection of various affected hormones, either alone (see, e.g., U.S. Pat. No. 7,348,137 (Caulfield, et al.), and U.S. Pat. No. 6,977,143 (Caulfield, et al.) describing detection of testosterone by mass spectrometric techniques; and U.S. patent application Ser. No. 12/207,482 (Ghoshal, et al.) describing detection of dehydroepiandrosterone (DHEA) by mass spectrometric techniques), or as part of a multi-analyte panel, have been disclosed in the art. For example, Carvalho, V., et al., *Chromatogr A* 2008, 872:154-61, reported a hormone panel which includes cortisol, 17-OH-progesterone, deoxycorticosterone, and 11-deoxycortisol by tandem mass spectrometry in serum; Guo, T., et al., *Clinica Chimica Acta* 2006, 372:76-82 reported a panel which includes cortisol, 11-deoxycortisol, androstenedione, testosterone, 17-OH-progesterone, DHEA, and progesterone in serum by HPLC-tandem mass spectrometry. Rauh, M., et al., *Steroids* 2006, 71:450-8, reported a panel which includes 17-OH progesterone, androstenedione, and testosterone by LC-tandem mass spectrometry for the diagnosis and monitoring of hyperandrogenic disorders. Janzen, M., et al., *J. Clin Endocrinol Metab* 2007, 92:2581-9, reported detection of a panel which included androstenedione, cortisol, 11-deoxycortisol, and 17-OH progesterone by tandem mass spectrometric techniques. Kushnir, M., et al., *Clinical Chemistry* 2006, 52:1559-67, reported detection of a panel which included derivatized forms of 11-deoxycortisol, 17-OH progesterone, 17-OH pregnenolone, and pregnenolone in blood by LC-tandem mass spectrometric techniques. Lacey, et al., *Clinical Chemistry* 2004, 50:621-5, and Minutti, C., et al., *J. Clin Endocrinol Metab* 2004, 89:3687-93, both reported detection of panels which included 17-OH progesterone, androstenedione, and cortisol by tandem mass spectrometric techniques. Shindo, N., et al., *Biomedical Chromatogr* 1990, 4:171-4, reported detection of a panel which included 17-OH progesterone, 11-deoxycortisol, progesterone, cortisol, testosterone, 17-OH pregnenolone and pregnenolone by plasmaspray LC-MS.

SUMMARY OF THE INVENTION

Methods are provided for detecting the amount of one or more CAH panel analytes (i.e., pregnenolone, 17-OH pregnenolone, progesterone, 17-OH progesterone, dehydroepiandrosterone (DHEA), androstenedione, testosterone, deoxycorticosterone, 11-deoxycortisol (also known as 11-desoxycortisol), cortisone, corticosterone, dihydrotestosterone, and cortisol) in a sample by mass spectrometry, including tandem mass spectrometry. In methods where amounts of multiple CAH panel analytes are detected, the amounts of multiple analytes are detected in the same sample injection.

These methods include: subjecting a sample, purified by methods described below, to an ionization source under conditions suitable to produce one or more ions detectable by mass spectrometry; determining the amounts of one or more ions from each of the one or more analytes by tandem mass spectrometry; and using the amounts of one or more ions from each of the one or more analytes to determine the amount of each one or more analyte in the sample. Preferably, the sample is a biological fluid; more preferably the sample is serum.

In some embodiments, the methods include detecting one or more analytes selected from the group consisting of pregnenolone and 17-OH pregnenolone. In some embodiments where the one or more analytes comprises pregnenolone, the one or more ions from pregnenolone comprise one or more ions selected from the group consisting of ions with a mass to charge ratio of 299.2, 105.6, and 91.1. In some embodiments where the one or more analytes comprises 17-OH pregnenolone, the one or more ions from 17-OH pregnenolone comprise one or more ions selected from the group consisting of ions with a mass to charge ratio of 297.2±0.5, 105.6±0.5, and 91.1±0.5. In some embodiments, both pregnenolone and 17-OH pregnenolone are determined.

In some embodiments, the methods also include (in addition to pregnenolone and 17-OH pregnenolone) determining the amount of one or more additional analytes in the sample selected from the group consisting of cortisol, cortisone, corticosterone, 11-deoxycortisol, testosterone, dehydroepiandrosterone (DHEA), deoxycorticosterone, androstenedione, 17-OH progesterone, and progesterone.

In preferred embodiments of the present invention, the amounts of two or more, three or more, four or more, five or more, six or more, seven or more, eight or more, nine or more, ten or more, eleven or more, twelve or more, or thirteen CAH panel analytes are determined.

In some embodiments, the levels of two or more CAH panel analytes are determined and at least one of the two or more analytes is selected from the group consisting of pregnenolone and 17-OH pregnenolone.

In some embodiments, one of two or more analytes is deoxycorticosterone, and a second of two or more analytes is selected from the group consisting of pregnenolone, 17-OH pregnenolone, progesterone, dehydroepiandrosterone (DHEA), androstenedione, and testosterone. In some embodiments where deoxycorticosterone is determined, the one or more ions from deoxycorticosterone comprise one or more ions selected from the group of ions with a mass to charge ratio of 331.2±0.5, 109.5±0.5, and 97.1±0.5.

In some embodiments, the sample has been purified by liquid chromatography prior to being subjected to an ionization source. In some embodiments, liquid chromatography may include one or more of high performance liquid chromatography, ultra high performance liquid chromatography, and turbulent flow liquid chromatography. In some embodiments, liquid chromatography is a combination of turbulent flow liquid chromatography and either high performance liquid chromatography or ultra high performance liquid chromatography.

In some embodiments, the one or more detected analytes are selected from the group consisting of pregnenolone, 17-OH pregnenolone, progesterone, 17-OH progesterone, dehydroepiandrosterone (DHEA), androstenedione, testosterone, deoxycorticosterone, 11-deoxycortisol, and cortisol, wherein if one or more detected analytes is only one analyte, the one analyte is not DHEA or testosterone. In these embodiments, the method includes the additional step of subjecting said sample to turbulent flow liquid chromatography to obtain a sample enriched in said one or more analytes subject to determination.

In a second aspect, methods are presented for diagnosing congenital adrenal hyperplasia (CAH), or some other condition affecting production of adrenal hormones. The methods for diagnosing include obtaining a sample of a body fluid from an individual suspected of having CAH and determining the level of two or more CAH panel analytes by tandem mass spectrometry.

In some of the CAH diagnosing embodiments, one of the two or more CAH panel analytes are selected from the group consisting of 17-OH pregnenolone, 17-OH progesterone, dehydroepiandrosterone (DHEA), androstenedione, deoxycorticosterone, and 11-deoxycortisol. In some related embodiments, the methods further include determining the ratio of the levels of one CAH panel analyte to another CAH panel analyte. In some embodiments, the ratio of the levels of 17-OH pregnenolone to 17-OH progesterone is determined. In the ratio of the levels of DHEA to androstenedione is determined.

Some embodiments of these methods may be used to diagnose a 21-hydroxylase deficiency form of CAH by determining an increased level of 17-OH progesterone over the level in a comparable body fluid sample from an individual without a 21-hydroxylase deficiency form of CAH. Some embodiments of these methods may be used to diagnose a 11-beta-hydroxylase deficiency form of CAH by determining increased levels of 11-deoxycortisol and deoxycorticosterone over the levels in a comparable body fluid sample from an individual without a 11-beta-hydroxylase deficiency form of CAH.

In some embodiments, one of the CAH panel analytes is pregnenolone. In related embodiments, one or more ions from pregnenolone comprise ions selected from the group consisting of ions with a mass to charge ratio (m/z) of 299.2±0.5, 105.6±0.5, and 91.1±0.5. In particularly preferred embodiments, one or more ions from pregnenolone comprise a precursor ion with m/z of 299.2±0.5, and one or more fragment ions selected from the group of ions with m/z of 105.6±0.5, and 91.1±0.5.

In some embodiments, one of the CAH panel analytes is 17-OH pregnenolone. In related embodiments, one or more ions from 17-OH pregnenolone comprise ions selected from the group consisting of ions with a mass to charge ratio (m/z) of 297.2±0.5, 105.6±0.5, and 91.1±0.5. In particularly preferred embodiments, one or more ions from 17-OH pregnenolone comprise a precursor ion with m/z of 297.2±0.5, and one or more fragment ions selected from the group of ions with m/z of 105.6±0.5 and 91.0±0.5.

In some embodiments, one of the CAH panel analytes is progesterone. In related embodiments, one or more ions from progesterone comprise ions selected from the group consisting of ions with a mass to charge ratio (m/z) of 315.2±0.5, 109.1±0.5, and 97.1±0.5. In particularly preferred embodiments, one or more ions from progesterone comprise a precursor ion with m/z of 315.2±0.5, and one or more fragment ions selected from the group of ions with m/z of 109.1±0.5 and 97.1±0.5.

In some embodiments, one of the CAH panel analytes is 17-OH progesterone. In related embodiments, one or more ions from 17-OH progesterone comprise ions selected from the group consisting of ions with a mass to charge ratio (m/z) of 331.0±0.5, 109.0±0.5, and 96.9±0.5. In particularly preferred embodiments, one or more ions from 17-OH progesterone comprise a precursor ion with m/z of 331.0±0.5, and one or more fragment ions selected from the group of ions with m/z of 109.0±0.5 and 96.9±0.5.

In some embodiments, one of the CAH panel analytes is DHEA. In related embodiments, one or more ions from DHEA comprise ions selected from the group consisting of ions with a mass to charge ratio (m/z) of 253.1±0.5, 197.1±0.5, and 157.1±0.5. In particularly preferred embodiments, one or more ions from DHEA comprise a precursor ion with m/z of 253.1±0.5, and one or more fragment ions selected from the group of ions with m/z of 197.1±0.5 and 157.1±0.5.

In some embodiments, one of the CAH panel analytes is androstenedione. In related embodiments, one or more ions from androstenedione comprise ions selected from the group consisting of ions with a mass to charge ratio (m/z) of 287.1±0.5, 109.1±0.5, and 91.1±0.5. In particularly preferred embodiments, one or more ions from androstenedione comprise a precursor ion with m/z of 287.1±0.5, and one or more fragment ions selected from the group of ions with m/z of 109.1±0.5, and 91.1±0.5.

In some embodiments, one of the CAH panel analytes is testosterone. In related embodiments, one or more ions from testosterone comprise ions selected from the group consisting of ions with a mass to charge ratio (m/z) of 289.1±0.5, 109.0±0.5, and 97.0±0.5. In particularly preferred embodiments, one or more ions from testosterone comprise a precursor ion with m/z of 289.1±0.5, and one or more fragment ions selected from the group of ions with m/z of 109.0±0.5 and 97.0±0.5.

In some embodiments, one of the CAH panel analytes is deoxycorticosterone. In related embodiments, one or more ions from deoxycorticosterone comprise ions selected from the group consisting of ions with a mass to charge ratio (m/z) of 331.2±0.5, 109.5±0.5, and 97.1±0.5. In particularly preferred embodiments, one or more ions from deoxycorticosterone comprise a precursor ion with m/z of 331.2±0.5, and one or more fragment ions selected from the group of ions with m/z of 109.5±0.5 and 97.1±0.5.

In some embodiments, one of the CAH panel analytes is 11-deoxycortisol (also known as 11-desoxycortisol). In related embodiments, one or more ions from 11-deoxycortisol comprise ions selected from the group consisting of ions with a mass to charge ratio (m/z) of 347.1±0.5, 109.1±0.5, and 97.1±0.5. In particularly preferred embodiments, one or more ions from 11-deoxycortisol comprise a precursor ion with m/z of 347.1±0.5, and one or more fragment ions selected from the group of ions with m/z of 109.1±0.5 and 97.1±0.5.

In some embodiments, one of the CAH panel analytes is dihydrotestosterone. In related embodiments, one or more ions from dihydrotestosterone comprise ions selected from the group consisting of ions with a mass to charge ratio (m/z) of 273.2±0.5, 105.1±0.5, and 91.1±0.5. In particularly preferred embodiments, one or more ions from dihydrotestosterone comprise a precursor ion with m/z of 273.2±0.5, and one or more fragment ions selected from the group of ions with m/z of 105.1±0.5 and 91.1±0.5.

In some embodiments, one of the CAH panel analytes is corticosterone. In related embodiments, one or more ions from corticosterone comprise ions selected from the group consisting of ions with a mass to charge ratio (m/z) of 347.2±0.5, 121.1±0.5, and 91.1±0.5. In particularly preferred embodiments, one or more ions from corticosterone comprise a precursor ion with m/z of 347.2±0.5, and one or more fragment ions selected from the group of ions with m/z of 121.1±0.5 and 91.1±0.5.

In some embodiments, one of the CAH panel analytes is cortisone. In related embodiments, one or more ions from cortisone comprise ions selected from the group consisting of ions with a mass to charge ratio (m/z) of 361.1±0.5, 163.2±0.5, and 105.1±0.5. In particularly preferred embodiments, one or more ions from cortisone comprise a precursor ion with m/z of 361.1±0.5, and one or more fragment ions selected from the group of ions with m/z of 163.2±0.5 and 105.1±0.5.

In some embodiments, one of the CAH panel analytes is cortisol. In related embodiments, one or more ions from cortisol comprise ions selected from the group consisting of ions with a mass to charge ratio (m/z) of 363.1±0.5, 121.0±0.5, and 90.9±0.5. In particularly preferred embodiments, one or more ions from cortisol comprise a precursor ion with m/z of 363.1±0.5, and one or more fragment ions selected from the group of ions with m/z of 121.0±0.5 and 90.9±0.5.

Embodiments of the present invention may involve the combination of liquid chromatography with mass spectrometry. In some embodiments, the liquid chromatography may comprise HPLC, UPLC, TFLC, or any combination thereof. For example, in some embodiments, HPLC, alone or in combination with one or more purification methods such as for example SPE (e.g., TFLC) and/or protein precipitation and filtration, is utilized to purify an analyte in a sample. In other embodiments, the liquid chromatography may comprise UPLC, either alone or in combination with one or more additional purification methods, such as SPE (e.g., TFLC) and/or protein precipitation and filtration, to purify an analyte in a sample.

In some embodiments, at least one purification step and mass spectrometric analysis is conducted in an on-line fashion. In another preferred embodiment, the mass spectrometry is tandem mass spectrometry (MS/MS).

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention.

In preferred embodiments, one or more separately detectable internal standards is provided in the sample, the amount of which is also determined in the sample. An internal standard may be used to account for loss of analytes during sample processing in order to get a more accurate value of a measured analyte in the sample. In these embodiments, all or a portion of one or more endogenous analytes selected from the group consisting of CAH panel analytes, and the one or more internal standards present in the sample are ionized to produce a plurality of ions detectable in a mass spectrometer. In preferred embodiments, the amount of ions generated from an analyte of interest may be related to the presence of amount of analyte of interest in the sample by comparison to one or more internal standards.

Preferred internal standards include $d_5$-testosterone, $d_4$-cortisol, and $d_9$-progestrone. However, these preferred internal standards is not intended to be exclusive, i.e., other suitable internal standards may be used. Isotopically labeled analogues of CAH panel analytes, such as $d_2$-11-deoxycortisol, $d_7$-androstenedione, $d_8$-17-OH progesterone, $d_2$-testosterone, and $d_2$-DHEA are also useful for use as internal standards.

In other embodiments, the amount of an analyte in a sample may be determined by comparison of the amount of one or more analyte ions detected by mass spectrometry to the amount of one or more standard ions detected by mass spectrometry in an external reference standard. Exemplary external reference standards may comprise blank plasma or serum spiked with a known amount of one or more of the above described internal standards and/or analytes of interest.

The features of the embodiments listed above may be combined without limitation for use in methods of the present invention.

As used herein, unless otherwise stated, the singular forms "a," "an," and "the" include plural reference. Thus, for example, a reference to "a protein" includes a plurality of protein molecules.

As used herein, an "isotopic label" produces a mass shift in the labeled molecule relative to the unlabeled molecule when analyzed by mass spectrometric techniques. Examples of suitable labels include deuterium, $^{13}C$, and $^{15}N$. Deuterium is a useful label because it can potentially produce three mass unit shifts in a labeled methylation product relative to an unlabeled methylation product. For example, $d_5$-testosterone has a mass five mass units higher than testosterone. An isotopic label may be incorporated at one or more positions in the molecule and one or more kinds of isotopic labels may be used on the same isotopically labeled molecule.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. Preferred samples for use in the present invention comprise human serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UPLC" or "UHPLC" (sometimes known as "ultra high pressure liquid chromatography") refers to HPLC which occurs at much higher pressures than traditional HPLC techniques.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow." When fluid flows slowly and smoothly, the flow is called "laminar flow." For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns," which have the general purpose of separating or extracting retained material from non-retained materials in order to obtain a purified sample for further analysis. As used in this context, the term "about" means±10%.

As used herein, the term "on-line" or "inline," for example as used in "on-line automated fashion" or "on-line extraction," refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "sample injection" refers to introducing an aliquot of a single sample into an analytical instrument, for example a mass spectrometer. This introduction may occur directly or indirectly. An indirect sample injection may be accomplished, for example, by injecting an aliquot of a sample into a HPLC or UPLC analytical column that is connected to a mass spectrometer in an on-line fashion.

As used herein, the term "same sample injection" with respect to multiple analyte analysis by mass spectrometry means that the ions for two or more different analytes are determined essentially simultaneously by measuring ions for the different analytes from the same (i.e. identical) sample injection.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIGS. 1A-M shows plots of elution profiles generated by HPLC-MS/MS analysis of various CAH panel analytes (cortisol, cortisone, corticosterone, 11-deoxycortisol, testosterone, DHEA, deoxycorticosterone, androstenedione, 17-OH progesterone, progesterone, dihydrotestosterone, pregnenolone, and 17-OH pregnenolone) in a patient sample. Details are discussed in Example 1.

FIGS. 15A-J show results of linearity studies for analysis of CAH panel analytes by HPLC-MS/MS. Details are described in Example 2.

DETAILED DESCRIPTION OF THE INVENTION

Figure 1M:
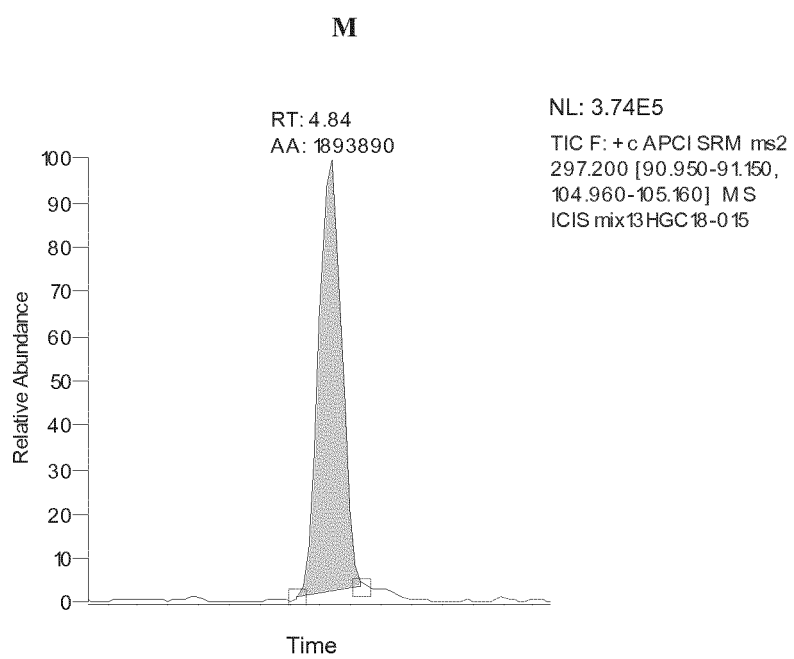

Methods are described for measuring the amount of one or more CAH panel analytes in a sample. More specifically, mass spectrometric methods are described for quantifying one or more CAH panel analytes in a sample that typically has been purified by one or more steps prior to mass spectrometry. The methods may utilize a liquid chromatography step such as HPLC to perform a purification of selected analytes combined with methods of mass spectrometry (MS) thereby providing a high-throughput assay system for quantifying one or more CAH panel analytes in a sample. The preferred embodiments are particularly well suited for application in large clinical laboratories for automated CAH monitoring.

Suitable samples for use in methods of the present invention include any sample that may contain one or more of the analytes of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as urine, blood, plasma, serum, saliva, and cerebrospinal fluid, or tissue samples; preferably plasma or serum; most preferably serum. Such samples may be obtained, for example, from a patient; that is, a living person, male or female, presenting oneself in a clinical setting for diagnosis, prognosis, or treatment of a disease or condition. The sample is preferably obtained from a patient, for example, a blood sample, which may be collected from a patient for removal as plasma or serum.

As used herein, "derivatizing" means reacting two molecules to form a new molecule. Thus, a derivatized analyte is a base molecule that has been reacted with another molecule for the purpose of, for example, facilitating purification, ionization, fragmentation, detection, or any combination thereof. In the methods described herein, the CAH panel analytes quantitated by mass spectrometry are preferably not derivatized.

The levels of circulating CAH panel analytes (determined by methods of the present invention) may be used to diagnose CAH, or some other condition affecting production of adrenal hormones, in an individual. The diagnosis of CAH depends is based on inadequate production of cortisol and aldosterone (or both) in conjunction with elevated concentrations of precursor hormones. For example, the 21-hydroxylase deficiency form of CAH can be detected by a high serum concentration of 17-hydroxyprogesterone (usually >1000 ng/dL) and urinary pregnanetriol (metabolite of 17-hydroxyprogesterone) in the presence of clinical features suggestive of the disease (e.g., salt wasting, clitoromegaly or ambiguous genitalia [in a female patient], precocious pubic hair, excessive growth, premature phallic enlargement in the absence of testicular enlargement, hirsutism, oligomenorrhea, female infertility).

In some embodiments, at least one of two or more determined CAH panel analytes are selected from the group consisting of 17-OH pregnenolone, 17-OH progesterone, dehydroepiandrosterone (DHEA), androstenedione, deoxycorticosterone, and 11-deoxycortisol. For example, CAH caused by 11-beta-hydroxylase deficiency can be detected by measuring elevated concentrations of 11-deoxycortisol and deoxycorticosterone or by an elevation in the ratio of a 24-hour urinary measurement of tetrahydrocompound S (metabolite of 11-deoxycortisol) to tetrahydrocompound F (metabolite of cortisol).

In some instances, it may be useful to determine a ratio of the levels of one CAH panel analyte to another in the sample. For example, 3-β-OH steroid dehydrogenase deficiency may be indicated by an abnormal ratio of 17-OH pregnenolone to 17-OH progesterone and/or an abnormal ratio of DHEA to androstenedione. In some embodiments, diagnostic methods of the present invention further comprise determining the ratio of the levels of one CAH panel analyte to another CAH panel analyte in the sample; preferably 17-OH pregnenolone to 17-OH progesterone, or DHEA to androstenedione. The determined ratios may then be compared to ratios of the same analytes in samples from individuals without CAH. Preferably the comparative samples are from normal, healthy individuals.

As used herein, "abnormal" indicates a state or condition that deviates from that observed a normal, healthy individual. Thus, an abnormal level or ratio represents a relative condition compared to that level or ratio observed in a health individual. One of skill in the art would be able to determine the degree of abnormality required to diagnose CAH in an individual.

The present invention also contemplates kits for a CAH diagnosis or monitoring assay. A kit for a CAH diagnosis or monitoring assay may include a kit comprising the compositions provided herein. For example, a kit may include packaging material and measured amounts of one or more isotopically labeled internal standards, in amounts sufficient for at least one assay. Typically, the kits will also include instructions recorded in a tangible form (e.g., contained on paper or an electronic medium) for using the packaged reagents for use in a CAH diagnosis or monitoring assay.

Sample Preparation for Mass Spectrometry

Some or all CAH panel analytes in a sample may be bound to proteins, if also present in the sample. Various methods may be used to disrupt the interaction between CAH panel analytes and protein prior to the implementation of one or more enrichment steps and/or MS analysis so that the amount of a CAH panel analyte measured by mass spectrometry is a reflection of the total for that CAH panel analyte in the sample. Once CAH panel analytes and proteins have been separated in the sample, CAH panel analytes may be enriched relative to one or more other components in the sample (e.g. protein) by various methods known in the art, such as for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a sample, especially a biological sample, such as serum or plasma. Such protein purification methods are well known in the art, for example, Polson et al., *Journal of Chromatography B* 785: 263-275 (2003), describes protein precipitation techniques suitable for use in the methods. Protein precipitation may be used to remove most of the protein from the sample leaving CAH panel analytes in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation obviates the need for turbulent flow liquid chromatography (TFLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or turbulent flow liquid chromatography (TFLC).

In other embodiments, CAH panel analytes may be released from a protein without having to precipitate the protein. For example, an aqueous formic acid solution may be added to the sample to disrupt interaction between a protein and a CAH panel analyte. Alternatively, ammonium sulfate or an aqueous solution of formic acid in ethanol may be added to the sample to disrupt ionic interactions between a carrier protein and a CAH panel analyte without precipitating the carrier protein.

In some preferred embodiments, TFLC, alone or in combination with one or more purification methods, may be used to purify CAH panel analytes prior to mass spectrometry. In such embodiments CAH panel analytes may be extracted using an TFLC extraction cartridge which captures the analytes, then eluted and chromatographed on a second TFLC column or onto an HPLC or UPLC analytical column prior to ionization. Because the steps involved in these chromatography procedures can be linked in an automated fashion, the requirement for operator involvement during the purification of the analyte can be minimized. This feature can result in savings of time and costs, and eliminate the opportunity for operator error.

It is believed that turbulent flow, such as that provided by TFLC columns and methods, may enhance the rate of mass transfer, improving separation characteristics. TFLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using TFLC columns is that the macromolecular build-up associated with biological fluid matrices is avoided since the high molecular weight species are not retained under the turbulent flow conditions. TFLC methods that combine multiple separations in one procedure lessen the need for lengthy sample preparation and operate at a significantly greater speed. Such methods also achieve a separation performance superior to laminar flow (HPLC) chromatography. TFLC often allows for direct injection of biological samples (plasma, urine, etc.). Direct injection is difficult to achieve in traditional forms of chromatography because denatured proteins and other biological debris quickly block the separation columns. TFLC also allows for very low sample volume of less than 1 mL, preferably less than 0.5 mL, preferably less than 0.2 mL, preferably about 0.1 mL.

Examples of TFLC applied to sample preparation prior to analysis by mass spectrometry have been described elsewhere. See, e.g., Zimmer et al., *J. Chromatogr*. A 854:23-35

(1999); see also, U.S. Pat. Nos. 5,968,367; 5,919,368; 5,795,469; and 5,772,874. In certain embodiments of the method, samples are subjected to protein precipitation as described above prior to loading on the TFLC column; in alternative preferred embodiments, the samples may be loaded directly onto the TFLC without being subjected to protein precipitation. Preferably, TFLC is used in conjunction with HPLC to extract and purify one or more CAH panel analytes without subjecting the sample to protein precipitation. In related preferred embodiments, purifying the sample prior to MS analysis involves (i) applying the sample to a TFLC extraction column, (ii) washing the TFLC extraction column under conditions whereby one or more HRT panel analytes are retained by the column, (iii) eluting retained CAH panel analytes from the TFLC extraction column, (iv) applying the retained material to an analytical column, and (v) eluting purified CAH panel analytes from the analytical column. The TFLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

One means of sample purification that may be used prior to mass spectrometry is liquid chromatography (LC). Certain LC techniques, including HPLC, rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process and may select HPLC instruments and columns that are suitable for use with CAH panel analytes. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups. The chromatographic column includes an inlet port for receiving a sample directly or indirectly from a solid-phase extraction or TFLC column and an outlet port for discharging an effluent that includes the fractionated sample.

In one embodiment, the sample is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted on a hydrophobic column chromatographic system. In certain preferred embodiments, TFLC and HPLC are performed using HPLC Grade organic and aqueous mobile phases. In some embodiments, the mobile phase may be 100% acetonitrile or methanol. In some embodiments, the aqueous mobile phase may be Ultra Pure water or an aqueous formic acid solution with a concentration between about 0.1% to about 20% formic acid.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of one or more CAH panel analytes prior to mass spectrometry. In such embodiments, one or more CAH panel analytes may be extracted using a TFLC extraction column, then eluted and chromatographed on a second TFLC column or onto an analytical HPLC column prior to ionization. For example, CAH panel analyte extraction with an TFLC extraction column may be accomplished with a large particle size (50 μm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, one or more CAH panel analytes may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

The one or more CAH panel analytes may be ionized in positive or negative mode to create one or more CAH panel ions. In some embodiments, the one or more CAH panel analytes are ionized by electrospray ionization (ESI) in positive or negative mode; preferably positive mode. In alternative embodiments, the one or more CAH panel analytes are ionized by atmospheric pressure chemical ionization (APCI)

in positive or negative mode; preferably positive mode. In related preferred embodiments, the one or more CAH panel ions are in a gaseous state and the inert collision gas is argon or nitrogen.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of one or more CAH analytes. Methods of generating and using such standard curves are well known in the art and one of ordinary skill is capable of selecting an appropriate internal standard. For example, in preferred embodiments one or more isotopically labeled analogues of CAH panel analytes (e.g., $d_5$-testosterone and $d_9$-progestrone) may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, one or more CAH panel analytes are quantified in a sample using MS/MS as follows. The samples are subjected to liquid chromatography, preferably TFLC followed by HPLC; the flow of liquid solvent from the chromatographic column enters the heated nebulizer interface of an MS/MS analyzer; and the solvent/analyte mixture is converted to vapor in the heated tubing of the interface. The CAH analytes contained in the nebulized solvent are ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of one of the CAH panel analytes. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral collision gas molecules and fragment. The fragment ions generated are passed into quadrupole 3 (Q3), where the fragment ions of the selected CAH panel analyte are selected while other ions are eliminated. During analysis of a single sample injection, Q1 and/or Q3 may be adjusted such that mass/charge ratios of one or more precursor ion/fragment ion pairs specific to one CAH panel analyte are first selected, followed at some later time by the selection of mass/charge ratios of one or more precursor ion/fragment ion pairs specific to a second CAH panel analyte, optionally repeated at some later time for as many CAH panel analytes as is desired. In particularly preferred embodiments, at least one precursor ion/fragment ion pair is selected for every CAH panel analyte in an analysis of a single sample injection, although the sequence of pair selection may occur in any order.

The methods may involve MS/MS performed in either positive or negative ion mode; preferably positive ion mode. Using standard methods well known in the art, one of ordinary skill is capable of identifying one or more fragment ions of a particular precursor ion of a CAH panel analyte that may be used for selection in quadrupole 3 (Q3). Preferred precursor ion/fragment ions for CAH panel analytes and exemplary internal standards are found in Table 1.

TABLE 1

Preferred Precursor Ion/Fragment Ion Mass to Charge Ratios of CAH Panel Analytes

| Analyte | Parent (m/z) | Fragment(s) (m/z) |
|---|---|---|
| cortisol | 363.1 ± 0.5 | 121.1 ± 0.5, 91.1 ± 0.5 |
| cortisone | 361.1 ± 0.5 | 163.2 ± 0.5, 105.1 ± 0.5 |
| corticosterone | 347.2 ± 0.5 | 121.1 ± 0.5, 91.1 ± 0.5 |
| 11-deoxycortisol | 347.1 ± 0.5 | 109.1 ± 0.5, 97.1 ± 0.5 |
| testosterone | 289.1 ± 0.5 | 109.0 ± 0.5, 97.0 ± 0.5 |
| DHEA | 253.1 ± 0.5 | 197.1 ± 0.5, 157.1 ± 0.5 |
| deoxycorticosterone | 331.2 ± 0.5 | 109.5 ± 0.5, 97.1 ± 0.5 |
| androstenedione | 287.1 ± 0.5 | 109.1 ± 0.5, 91.1 ± 0.5 |
| 17-OH progesterone | 331.0 ± 0.5 | 109.0 ± 0.5, 96.9 ± 0.5 |
| progesterone | 315.2 ± 0.5 | 109.1 ± 0.5, 97.1 ± 0.5 |
| dihydrotestosterone | 273.2 ± 0.5 | 105.1 ± 0.5, 91.1 ± 0.5 |
| pregnenolone | 299.2 ± 0.5 | 105.6 ± 0.5, 91.1 ± 0.5 |
| 17-OH pregnenolone | 297.2 ± 0.5 | 105.6 ± 0.5, 91.1 ± 0.5 |

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of each CAH panel analyte detected. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods.

EXAMPLES

Example 1

Extraction of CAH Panel Analytes from Samples Using LC

Liquid chromatography was performed on purified samples made from 100-200 µL serum.

A binary HPLC gradient of an aqueous phase (i.e., mobile phase A) and an organic phase (i.e., mobile phase B) was applied to the analytical column to separate CAH panel analytes from each other and other analytes contained in the sample. The gradient starts at 85% mobile phase A/15% mobile phase B and ramps to 25% mobile phase A/75% mobile phase B over 50 seconds. The approximate retention times of the various CAH panel analytes are shown in Table 2.

TABLE 2

Approximate Retention Times of CAH Panel Analytes

| Analyte | Approximate Retention Time (min) |
|---|---|
| cortisol | 2.74 |
| cortisone | 2.76 |
| corticosterone | 2.93 |
| 11-deoxycortisol | 2.97 |
| testosterone | 3.37 |
| DHEA | 3.54 |
| androstenedione | 3.54 |
| deoxycorticosterone | 3.55 |
| 17-OH progesterone | 3.55 |
| progesterone | 4.80 |
| dihydrotestosterone | 4.83 |
| pregnenolone | 4.83 |
| 17-OH pregnenolone | 4.84 |

Exemplary chromatograms of the resulting separated analytes are demonstrated in FIGS. 1A-M for cortisol, cortisone, corticosterone, 11-deoxycortisol, testosterone, DHEA, deoxycorticosterone, androstenedione, 17-OH progesterone, progesterone, dihydrotestosterone, pregnenolone, and 17-OH pregnenolone, respectively. It should be noted that in FIGS. 1H and 1I for androstenedione and 17-OH progesterone, respectively, an erroneous chromatographic peak was observed. These peaks are labeled in the Figures with an X.

These separated samples were then subjected to MS/MS for quantitation of selected CAH panel analytes.

Example 2

Quantitation of CAH Panel Analytes by MS/MS

MS (and MS/MS) was performed on separated samples generated above by first generating ions from the sample. These ions were passed to the first quadrupole (Q1), which selected ions with a desired parent mass to charge ratio. Ions entering Quadrupole 2 (Q2) collided with argon gas to generate ion fragments, which were passed to quadrupole 3 (Q3) for further selection. Simultaneously, the same process using isotope dilution mass spectrometry was carried out with selected isotope-labeled internal standards. All of the selected masses for each CAH panel analyte are listed in Table 1, above.

FIGS. 2-14 show mass spectra resulting from fragmentation of the precursor ions indicated in Table 1.

Figure 2:
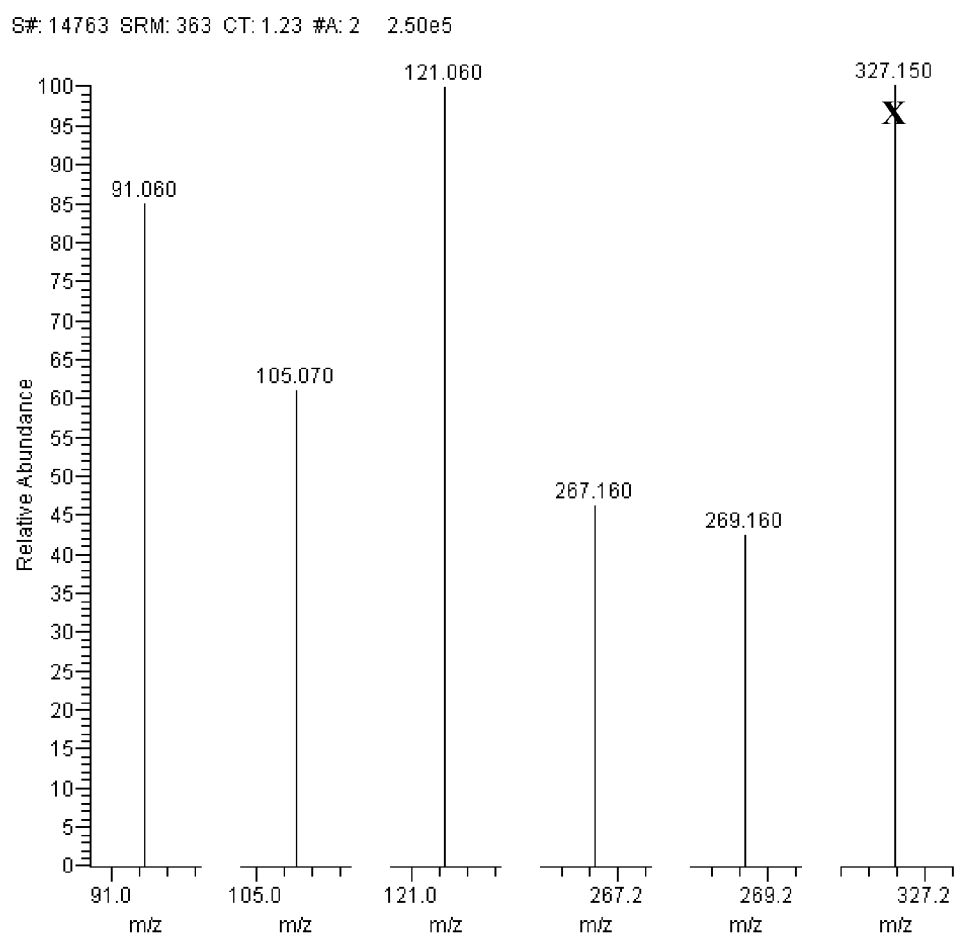
FIG. 2 shows product ion peaks generated from tandem mass spectrometric fragmentation of cortisol (precursor ion of about 363.1±0.5). Details are described in Example 2.

As seen in FIG. 2, exemplary MRM transitions that may be monitored for the quantitation of cortisol include fragmenting a precursor ion with a m/z of about 363.1±0.5 to product ions with m/z of about 121.0±0.5 and 90.9±0.5. A fragment was also observed at a mass to charge ratio of about 327±0.5 that was not believed to be suitable for quantitation of cortisol. This fragment is indicated in FIG. 2 with an X.

Figure 3:
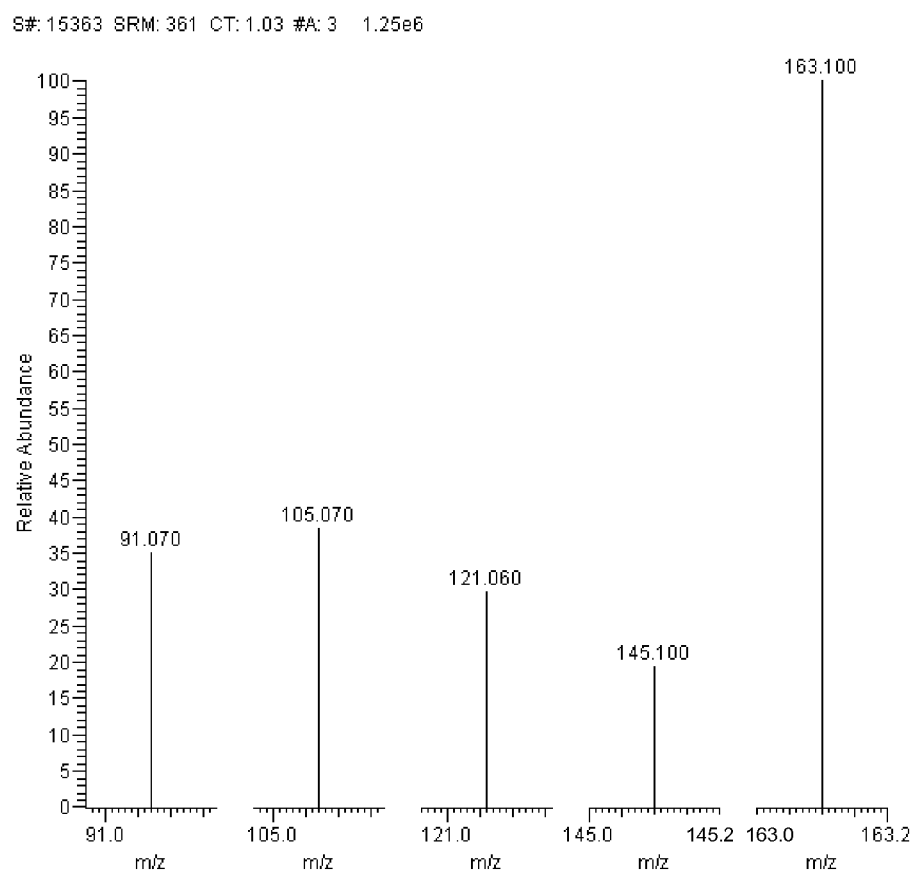
FIG. 3 shows product ion peaks generated from tandem mass spectrometric fragmentation of cortisone (precursor ion of about 361.1±0.5). Details are described in Example 2.

As seen in FIG. 3, exemplary MRM transitions that may be monitored for the quantitation of cortisone include fragmenting a precursor ion with a m/z of about 361.1±0.5 to product ions with m/z of about 163.2±0.5 and 105.1±0.5.

Figure 4:
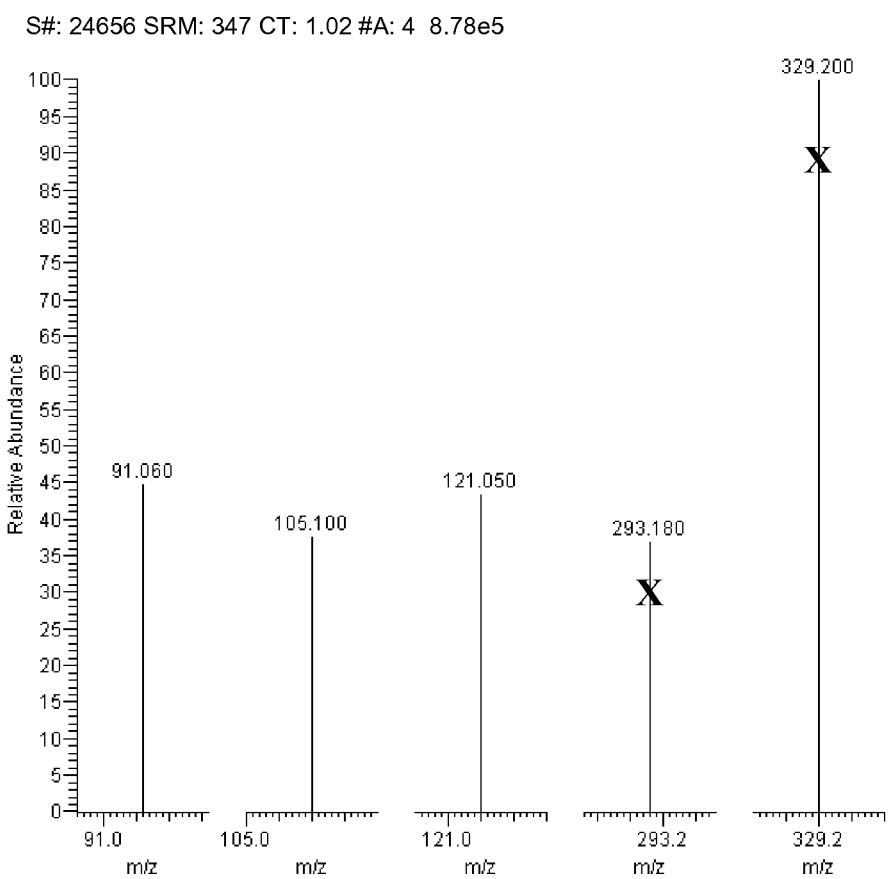
FIG. 4 shows product ion peaks generated from tandem mass spectrometric fragmentation of corticosterone (precursor ion of about 347.2±0.5). Details are described in Example 2.

As seen in FIG. 4, exemplary MRM transitions that may be monitored for the quantitation of corticosterone include fragmenting a precursor ion with a m/z of about 347.2±0.5 to product ions with m/z of about 121.1±0.5 and 91.1±0.5. Two fragments were also observed at mass to charge ratios of about 329±0.5 and 293±0.5 that were not believed to be suitable for quantitation of corticosterone. These fragments are indicated in FIG. 4 with an X.

Figure 5:
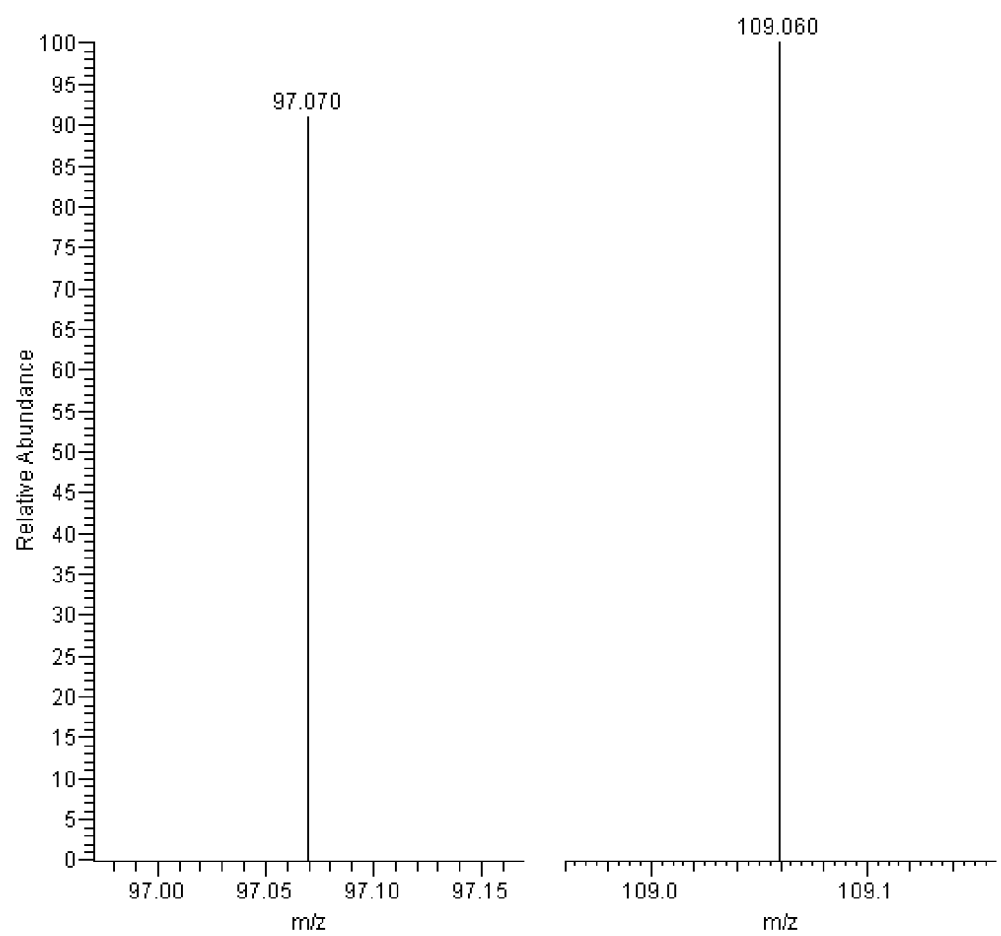
FIG. 5 shows product ion peaks generated from tandem mass spectrometric fragmentation of 11-deoxycortisol (precursor ion of about 347.1±0.5). Details are described in Example 2.

As seen in FIG. 5, exemplary MRM transitions that may be monitored for the quantitation of 11-deoxycortisol include fragmenting a precursor ion with a m/z of about 347.1±0.5 to product ions with m/z of about 109.1±0.5 and 97.1±0.5.

Figure 6:
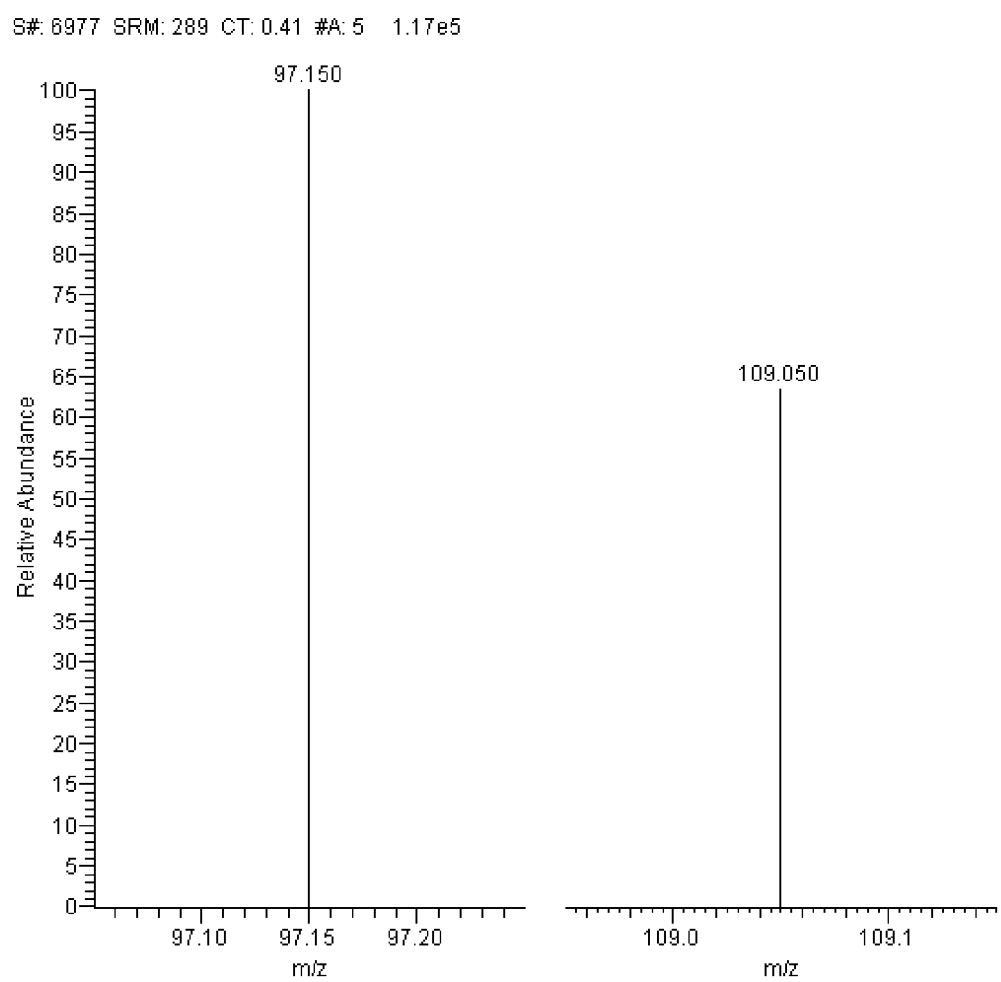
FIG. 6 shows product ion peaks generated from tandem mass spectrometric fragmentation of testosterone (precursor ion of about 289.1±0.5). Details are described in Example 2.

As seen in FIG. 6, exemplary MRM transitions that may be monitored for the quantitation of testosterone include fragmenting a precursor ion with a m/z of about 289.1±0.5 to product ions with m/z of about 109.0±0.5 and 97.0±0.5.

Figure 7:
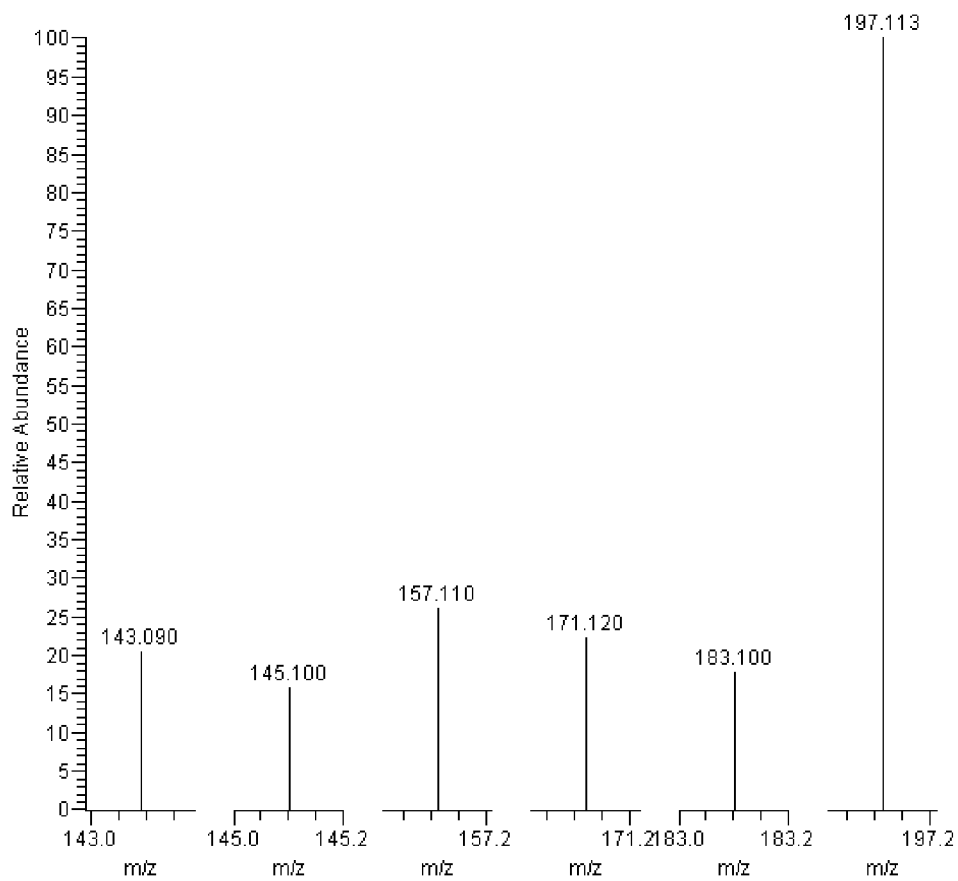
FIG. 7 shows product ion peaks generated from tandem mass spectrometric fragmentation of DHEA (precursor ion of about 253.1±0.5). Details are described in Example 2.

As seen in FIG. 7, exemplary MRM transitions that may be monitored for the quantitation of DHEA include fragmenting a precursor ion with a m/z of about 253.1±0.5 to product ions with m/z of about 197.1±0.5 and 157.1±0.5.

Figure 8:
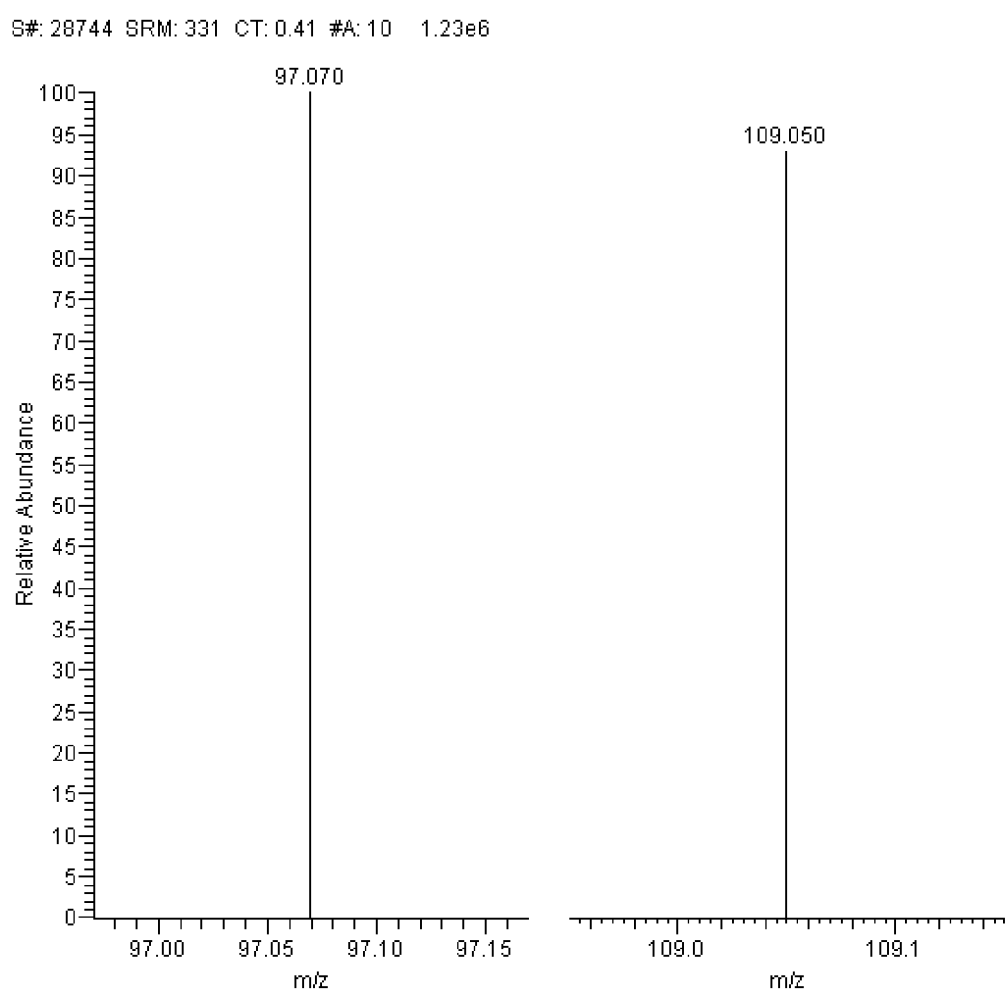
FIG. 8 shows product ion peaks generated from tandem mass spectrometric fragmentation of deoxycorticosterone (precursor ion of about 331.2±0.5). Details are described in Example 2.

As seen in FIG. 8, exemplary MRM transitions that may be monitored for the quantitation of deoxycorticosterone include fragmenting a precursor ion with a m/z of about 331.2±0.5 to product ions with m/z of about 109.5±0.5 and 97.1±0.5.

Figure 9:
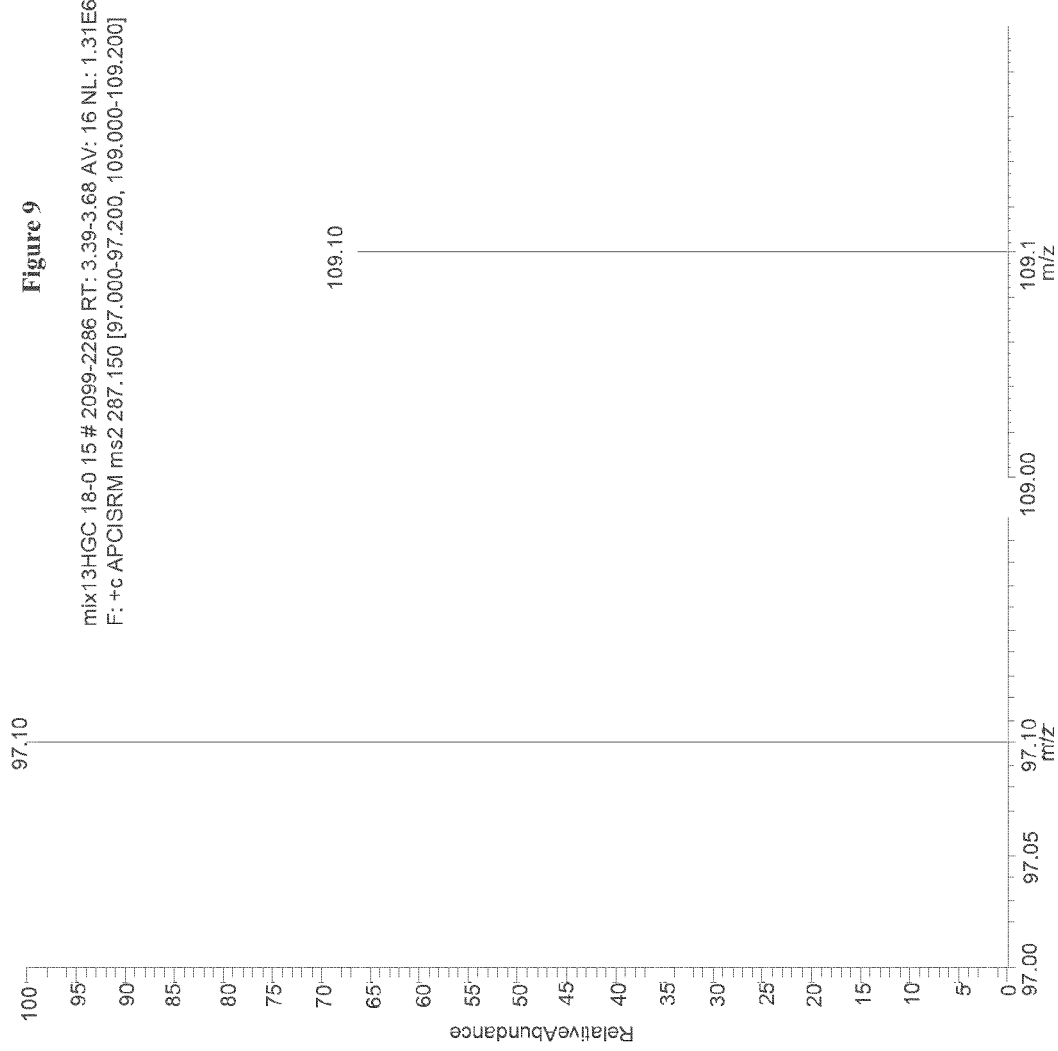
FIG. 9 shows product ion peaks generated from tandem mass spectrometric fragmentation of androstenedione (precursor ion of about 287.1±0.5). Details are described in Example 2.

As seen in FIG. 9, exemplary MRM transitions that may be monitored for the quantitation of androstenedione include fragmenting a precursor ion with a m/z of about 287.1±0.5 to product ions with m/z of about 109.1±0.5 and 91.1±0.5.

Figure 10:
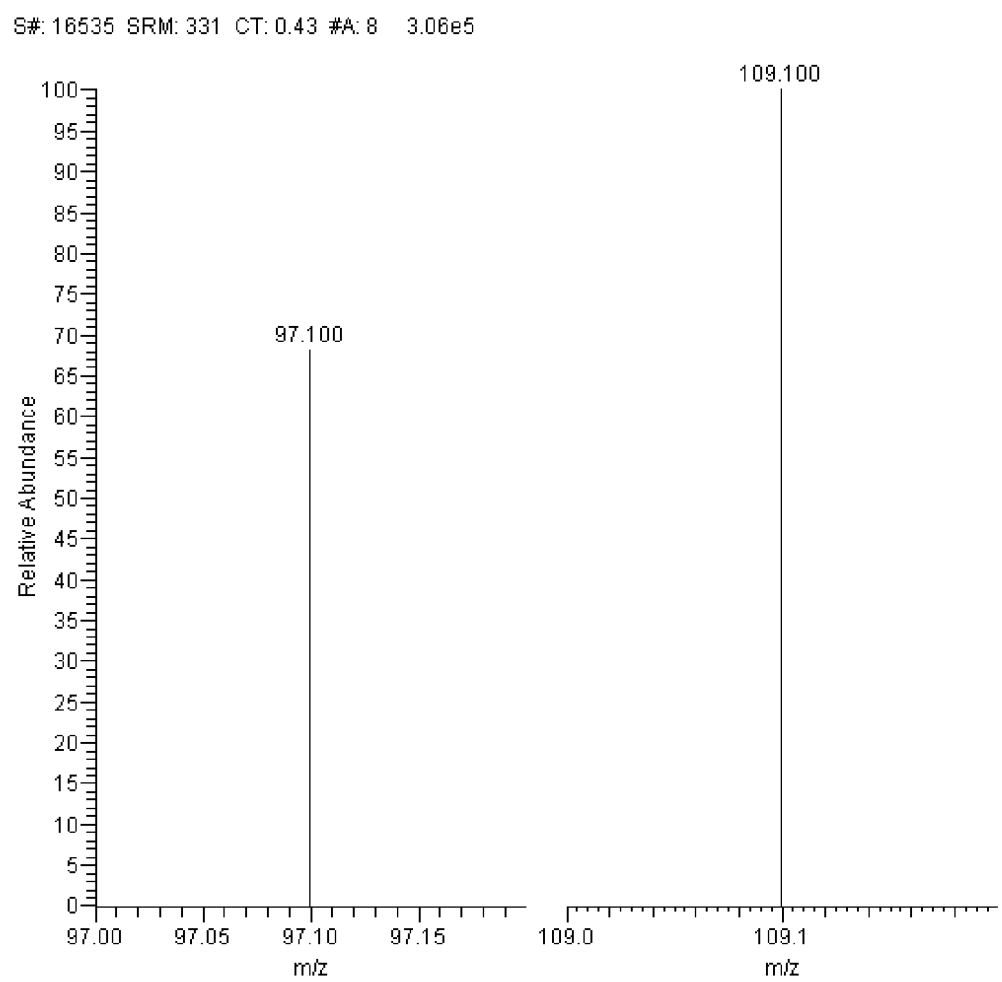
FIG. 10 shows product ion peaks generated from tandem mass spectrometric fragmentation of 17-OH progesterone (precursor ion of about 331.0±0.5). Details are described in Example 2.

As seen in FIG. 10, exemplary MRM transitions that may be monitored for the quantitation of 17-OH progesterone include fragmenting a precursor ion with a m/z of about 331.0±0.5 to product ions with m/z of about 109.0±0.5 and 96.9±0.5.

Figure 11:
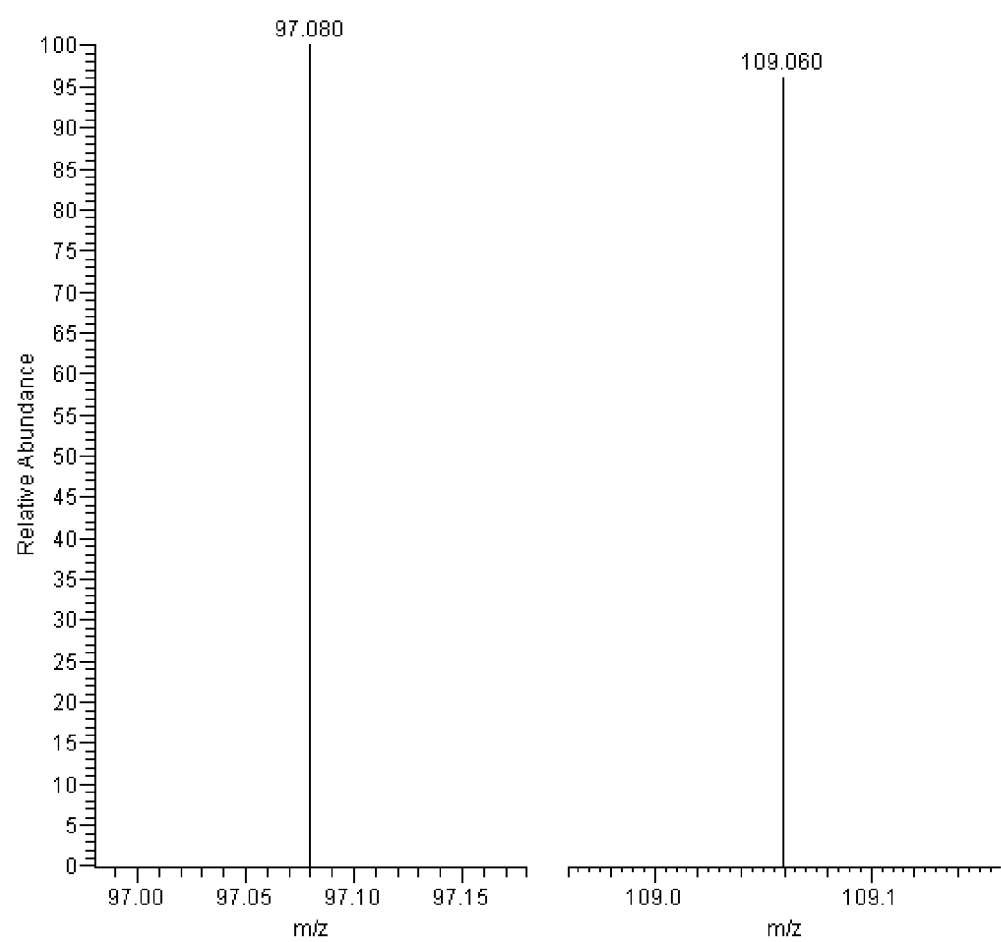
FIG. 11 shows product ion peaks generated from tandem mass spectrometric fragmentation of progesterone (precursor ion of about 315.2±0.5). Details are described in Example 2.

As seen in FIG. 11, exemplary MRM transitions that may be monitored for the quantitation of progesterone include fragmenting a precursor ion with a m/z of about 315.2±0.5 to product ions with m/z of about 109.1±0.5 and 97.1±0.5.

Figure 12:
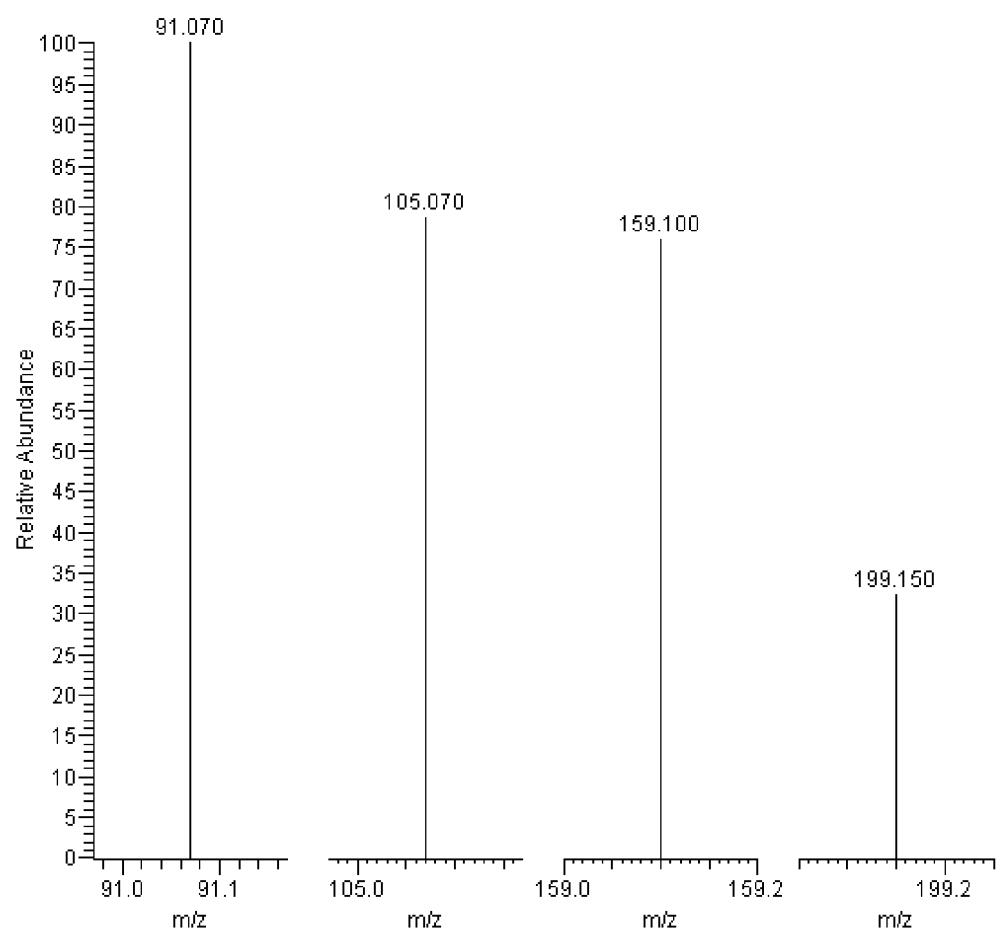
FIG. 12 shows product ion peaks generated from tandem mass spectrometric fragmentation of dihydrotestosterone (precursor ion of about 273.2±0.5). Details are described in Example 2.

As seen in FIG. 12, exemplary MRM transitions that may be monitored for the quantitation of dihydrotestosterone include fragmenting a precursor ion with a m/z of about 273.2±0.5 to product ions with m/z of about 105.1±0.5 and 91.1±0.5.

Figure 13:
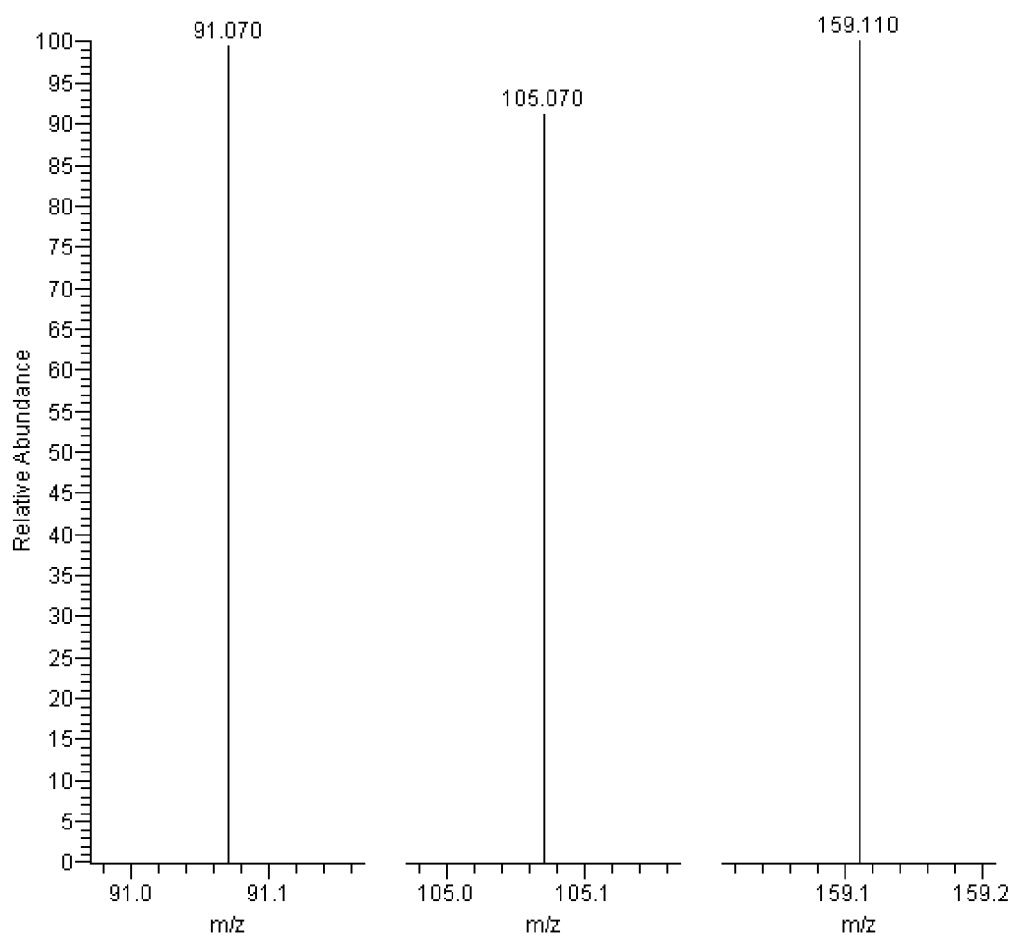
FIG. 13 shows product ion peaks generated from tandem mass spectrometric fragmentation of pregnenolone (precursor ion of about 299.2±0.5). Details are described in Example 2.

As seen in FIG. 13, exemplary MRM transitions that may be monitored for the quantitation of pregnenolone include fragmenting a precursor ion with a m/z of about 299.2±0.5 to product ions with m/z of about 105.6±0.5 and 91.1±0.5.

Figure 14:
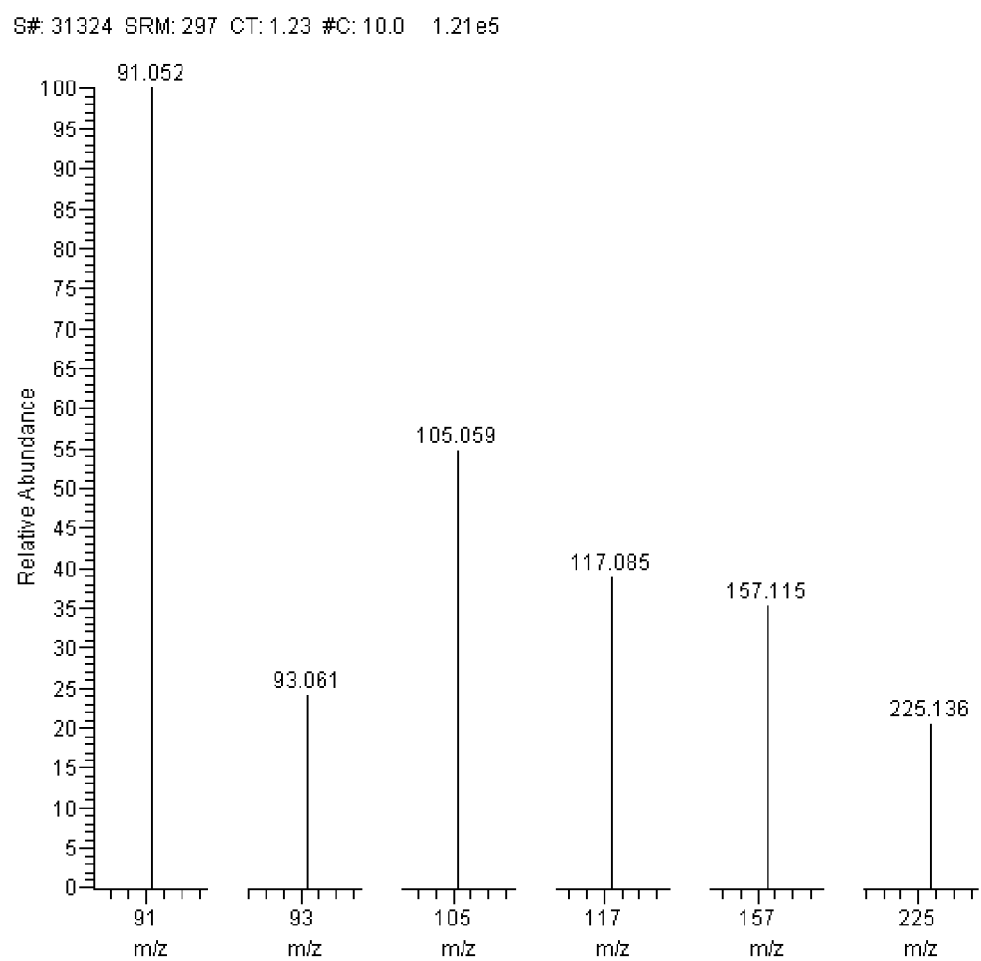
FIG. 14 shows product ion peaks generated from tandem mass spectrometric fragmentation of 17-OH pregnenolone (precursor ion of about 297.2±0.5). Details are described in Example 2.

As seen in FIG. 14, exemplary MRM transitions that may be monitored for the quantitation of 17-OH pregnenolone include fragmenting a precursor ion with a m/z of about 297.2±0.5 to product ions with m/z of about 105.6±0.5 and 91.1±0.5.

As can be seen in the product ion scans in FIGS. 2-14, several other product ions are generated upon fragmentation of the indicated precursor ions. Any of the additional product ions indicated in FIGS. 2-14 may be selected to replace or augment the exemplary fragment ions described above and in Table 1.

Linearity studies were conducted for detection of cortisol, 11-deoxycortisol, androstenedione, deoxycorticosterone, 17-OH-progesterone, 17-OH-pregnenolone, testosterone, progesterone, pregnenolone, and DHEA across a range of concentrations for each analyte of approximately 0 ng/dL to 1000 ng/dL. Results of these studies are presented in FIGS. 3 A-J, respectively.

The limits of quantitation of the CAH panel analyte were determined (for each individual analyte except deoxycorticosterone, and for each analyte as part of a 10 member panel). Results of these studies are presented in Table 3, below.

TABLE 3

Limits of Quantitation for CAH Panel Analytes, Individually and Within a Panel

| Analyte | Individual LOQ (ng/dL) | Panel LOQ (ng/dL) |
|---|---|---|
| cortisol | 100.0 | 50.0 |
| 11-deoxycortisol | 20.0 | 20.0 |
| testosterone | 2.0 | 10.0 |
| DHEA | 10.0 | 15.0 |
| deoxycorticosterone | — | 25.0 |

TABLE 3-continued

Limits of Quantitation for CAH Panel Analytes, Individually and Within a Panel

| Analyte | Individual LOQ (ng/dL) | Panel LOQ (ng/dL) |
|---|---|---|
| androstenedione | 5.0 | 10.0 |
| 17-OH progesterone | 8.0 | 20.0 |
| progesterone | 10.0 | 10.0 |
| pregnenolone | 5.0 | 15.0 |
| 17-OH pregnenolone | 6.0 | 15.0 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining in a sample, by mass spectrometry, the amounts of at least three analytes selected from the group consisting of pregnenolone, 17-OH pregnenolone, progesterone, 17-OH progesterone, dehydroepiandrosterone (DHEA), androstenedione, testosterone, 11-deoxycortisol, deoxycorticosterone, and cortisol, the method comprising:
    subjecting the sample to an ionization source under conditions suitable to produce one or more ions detectable by mass spectrometry from each of the analytes, wherein the analytes are not derivatized prior to ionization;
    determining, by tandem mass spectrometry, the amounts of the one or more ions from each of the analytes; and using the determined amounts of the one or more ions to determine the amount of each of the analytes in the sample.

2. The method of claim 1, wherein the analytes comprise cortisol, androstenedione and 17-OH progesterone.

3. The method of claim 2, wherein the sample comprises plasma or serum.

4. The method of claim 1, wherein the analytes comprise cortisol, androstenedione and progesterone.

5. The method of claim 4, wherein the sample comprises plasma or serum.

6. The method of claim 1, wherein the analytes comprise cortisol, deoxycorticosterone and 17-OH progesterone.

7. The method of claim 6, wherein the sample comprises plasma or serum.

8. The method of claim 1, wherein the analytes comprise testosterone, androstenedione and dehydroepiandrosterone (DHEA).

9. The method of claim 8, wherein the sample comprises plasma or serum.

10. The method of claim 1, wherein the analytes comprise four or more analytes.

11. The method of claim 1, wherein the analytes comprise five or more analytes.

12. The method of claim 1, wherein the sample has been purified by liquid chromatography prior to being subjected to an ionization source.

13. The method of claim 12, wherein said liquid chromatography is selected from the group consisting of high performance liquid chromatography, ultra high performance liquid chromatography, and turbulent flow liquid chromatography.

14. The method of claim 1, wherein the sample has been purified by turbulent flow liquid chromatography and either high performance liquid chromatography or ultra high performance liquid chromatography prior to being subjected to an ionization source.

15. The method of claim 1, wherein an internal standard is used for determination of the amounts of the analytes in the sample.

16. The method of claim 15, wherein the internal standard comprises an isotopically labeled analogue of one of the analytes.

17. The method of claim 1, wherein the sample comprises a biological sample.

18. A kit for a congenital adrenal hyperplasia (CAH) diagnosis or monitoring comprising one or more isotopically labeled analogues as internal standards for each of three analytes selected from the group consisting of pregnenolone, 17-OH pregnenolone, progesterone, 17-OH progesterone, dehydroepiandrosterone (DHEA), androstenedione, testosterone, 11-deoxycortisol, deoxycorticosterone, and cortisol, packaging material and instructions for using the kit for CAH diagnosis or monitoring.

19. The kit of claim 18, wherein the internal standards comprises three or more selected from the group consisting of $d_5$-testosterone, $d_4$-cortisol, $d_9$-progestrone, $d_2$-11-deoxycortisol, $d_7$-androstenedione, $d_8$-17-OH progesterone, $d_2$-testosterone, and $d_2$-DHEA.

20. The kit of claim 18, wherein the internal standards comprises $d_5$-testosterone, $d_4$-cortisol and $d_9$-progestrone.

* * * * *